(12) United States Patent
Mukherjee et al.

(10) Patent No.: US 12,302,905 B1
(45) Date of Patent: May 20, 2025

(54) FIELD-DEPLOYABLE ANTIMICROBIAL PRODUCT ASSEMBLIES FOR AIR AND WATER PURIFICATION AND METHODS OF FABRICATION OF THE SAME

(71) Applicant: Kavach Nanotechnologies Inc., Fremont, CA (US)

(72) Inventors: Niloy Mukherjee, San Ramon, CA (US); Somilkumar J. Rathi, Fremont, CA (US); Aditi Mukherjee, San Ramon, CA (US); John Surma, Los Gatos, CA (US); Jose Rafael Alva, San Jose, CA (US); Veljibhai B. Patel, Folsom, CA (US); Jagdishchandra A. Rathi, Fremont, CA (US)

(73) Assignee: Kavach Nanotechnologies Inc., Fremont, CA (US)

( * ) Notice: Subject to any disclaimer, the term of this patent is extended or adjusted under 35 U.S.C. 154(b) by 0 days.

(21) Appl. No.: 18/775,198

(22) Filed: Jul. 17, 2024

(51) Int. Cl.
| | |
|---|---|
| *B01D 46/00* | (2022.01) |
| *A01N 25/08* | (2006.01) |
| *A01N 59/16* | (2006.01) |
| *A01N 59/20* | (2006.01) |
| *A01P 1/00* | (2006.01) |
| *A61L 9/00* | (2006.01) |
| *B01D 29/00* | (2006.01) |
| *B01D 53/22* | (2006.01) |
| *B01D 61/00* | (2006.01) |
| *C02F 1/50* | (2023.01) |
| *C23C 16/455* | (2006.01) |
| *C23C 16/56* | (2006.01) |

(Continued)

(52) U.S. Cl.
CPC ............ *A01N 59/20* (2013.01); *A01N 25/08* (2013.01); *A01N 59/16* (2013.01); *A01P 1/00* (2021.08); *A61L 9/00* (2013.01); *C02F 1/505* (2013.01); *C23C 16/45555* (2013.01); *C23C 16/56* (2013.01); *C23C 28/00* (2013.01); *C25D 11/04* (2013.01); *C25D 11/18* (2013.01); *A61L 2101/24* (2020.08); *A61L 2101/26* (2020.08); *C02F 1/281* (2013.01); *C02F 2303/04* (2013.01); *C23C 16/00* (2013.01)

(58) Field of Classification Search
CPC .......... H01L 21/7685; H01L 21/28518; B01D 71/02; C25B 9/10; C02F 9/00
USPC ................ 210/490, 650; 96/11, 121; 95/278
See application file for complete search history.

(56) References Cited

U.S. PATENT DOCUMENTS 8,448,790 B2 * 5/2013 Cotte ................. B01D 67/0065
210/500.21

* cited by examiner

*Primary Examiner* — Monzer R Chorbaji
(74) *Attorney, Agent, or Firm* — PatentPC/PowerPatent; Bao Tran

(57) ABSTRACT

Despite the existence and deployment of a range of antimicrobial/disinfectant/sterilization technologies and products, transmission of infectious diseases remains a significant problem worldwide, continuing to cause hundreds of millions of infections and millions of deaths every year of both human beings and animals. State-of-the-art technologies suffer from several disadvantages including being discrete in space and time, being overly dependent on human skill and discipline, and in some cases having harmful side-effects to human health. This invention proposes a series of industrial grade antimicrobial product designs, and materials and methods to make them highly effective products that offer continuous antimicrobial action, with minimum dependence on human discipline and skill once deployed, and with no harmful side-effects.

20 Claims, 16 Drawing Sheets

(51) Int. Cl.
  *C23C 28/00* (2006.01)
  *C25D 11/04* (2006.01)
  *C25D 11/18* (2006.01)
  *A61L 101/24* (2006.01)
  *A61L 101/26* (2006.01)
  *C02F 1/28* (2023.01)
  *C23C 16/00* (2006.01)

FIELD-DEPLOYABLE ANTIMICROBIAL PRODUCT ASSEMBLIES FOR AIR AND WATER PURIFICATION AND METHODS OF FABRICATION OF THE SAME

CROSS-REFERENCE OF RELATED APPLICATIONS

None at this time.

BACKGROUND

Despite the existence and deployment of a range of antimicrobial/disinfectant/sterilization technologies and products, transmission of infectious diseases remains a significant problem worldwide, continuing to cause hundreds of millions of infections and millions of deaths every year of both human beings and animals. State-of-the-art technologies suffer from several disadvantages including being discrete in space and time, being overly dependent on human skill and discipline, and in some cases having harmful side-effects to human health.

This disclosure teaches, describes and suggests a series of industrial grade antimicrobial product designs, and materials and methods to make them highly effective products that offer continuous antimicrobial action, with minimum dependence on human discipline and skill once deployed, and with no harmful side-effects.

This disclosure describes designs and methods of fabrication of field-deployable products for the inactivation of harmful microorganisms in air and liquid (such as water) and fluid more effectively than the current state-of-the-art technologies.

The types of microorganisms targeted include bacteria, viruses, fungi, mold, protozoa and bacterial toxins harmful to human and animal health. Also targeted are airborne volatile organic compounds that are or may be harmful to human and animal health.

Embodiments of this invention makes use of antimicrobial materials, describing methods to fabricate and incorporate such materials onto surfaces, and methods to optimize the material fabrication processes to obtain highly reactive such antimicrobial surfaces. Described are advanced nanostructure fabrication methods of semiconducting and metallic materials that lead to extremely high antimicrobial efficacy.

This disclosure also teaches, describes, and suggests designs and other structural aspects of product assemblies incorporating such antimicrobial surfaces, the field-deployable nature of the product assemblies, as well as methods and embodiments to make them more effective.

The state-of-the art antimicrobial/germicidal/disinfection/sterilization technologies prevalent today are:

Air purification: For example, some air purification products made by the company Molekule. These types of products typically use one or more of the following technologies:

HEPA (high-efficiency particulate air) filters: mechanical filtration to remove airborne particles including microbes of certain size ranges. HEPA filters usually employ only mechanical trapping; there is no chemical/germicidal action.

HEGA (high-efficiency gas adsorption) filters: adsorption-based filters which remove harmful gases and VOCs (Volatile Organic Compounds). They are not antimicrobial.

PCO (photochemical oxidation) filters: antimicrobial & anti-VOC filters.

Small scale water purification: Some of the water purification products made for the consumer market use UV radiation (UV germicidal irradiation, UVGI), and others that use mechanical filtration techniques/assemblies.

Large scale water purification: Though both UVGI and chemical additives (e.g., chlorine) are often used for large scale water purification, the inventors are not aware of any products for large scale water purification that use the technologies taught in this disclosure.

Despite the advent of many antimicrobial products, in addition to vaccines and medicines, the spread of infectious diseases continue to pose a major challenge to human civilization and animal welfare, as evidenced by the recent COVID-19 pandemic and scores of other recent outbreaks and epidemics among both human and animal populations. The staggering loss of life, human and animal suffering, and the resulting colossal economic damage are a wake-up call to society. More innovative products are needed to improve our ability to prevent the spread of infectious diseases.

For air purification: [a] Filtration, including HEPA (high-efficiency particulate air) and HEGA (high-efficiency gas adsorption) filters; and [b] Ultraviolet germicidal irradiation (UVGI); [c] Photochemical Oxidation (PCO) filters.

For liquid (such as water) purification: [a] Filtration; [b] Chemical additives (e.g. Chlorine); and [c] UVGI.

For surfaces (non-skin): [a] Chemical treatments (e.g., hydrogen peroxide, bleach); and [b] UVGI.

Most of the above technologies have one or more of the following disadvantages. It is primarily due to these disadvantages that, despite the deployment of these technologies, the spread of infectious diseases continue to plague society.

Discrete application: Only used at discrete points in space and time. This is the case with all filtration products (discrete in space). This is also the case with the timing/frequency of application, e.g., hospital staff may disinfect surfaces only once a day (discrete in time) for example.

Human-discipline and skill dependent: Currently, products rely on human discipline and skill for efficacy. For example, [a] filters get clogged and become ineffective unless they are replaced at recommended frequencies; and [b] The efficacy of chemical disinfectants relies on a human being's discipline and skill for timely and effective application.

Some well-known health problems due to above disadvantages of existing technologies are:

Mold (a type of fungi) and bacterial infestation in household HVAC systems and their resultant harmful effects on human health are well known problems; these typically happen within HVAC ducting, downstream, upstream, and within filters.

Healthcare Associated Infections (HAIs) are another well-known problem worldwide that, according to the World Health Organization, affect up to 15% of ICU patients. Ventilator-associated Pneumonia (VAP) is one prevalent type of HAI; once again this occurs primarily due to the growth of bacteria in hospital HVAC ducting despite the deployment of existing filtration and UVGI technologies in many cases. Another major cause of HAIs is lack of training and discipline among healthcare practitioners, which leads to improper disinfection of invasive instruments such as catheters and improper surgical procedures, which in turn cause infections in patients.

Diarrhea, a water-borne infectious disease caused by Norovirus, remains a major worldwide public health problem, causing an estimated 1.5 million deaths every year. It is the second leading cause of death among children under the age of 5; >400,000 children die of diarrhea every year per the UNICEF and WHO. However, diarrhea is largely preventable. It is obvious from the facts that additional antimicrobial technologies, and a more widespread deployment of such technologies, are required to minimize the staggering death toll and human suffering from diarrhea and other water-borne infectious diseases.

Perhaps a less well-known problem is the advent of bacterial and viral epidemics among fish. With the advent of more and more fish farms worldwide, this issue is becoming more prevalent. Overcrowding conditions in man-made fish farms can lead to epidemics, which necessitate widespread euthanasia of fish to prevent the infection from spreading to human populations. The resulting economic effects on fish farms can be devastating.

Harmful side-effects: Another disadvantage of several state-of-the-art chemical treatment technologies, e.g., chemical additives such as chlorine, hydrogen peroxide, bleach, etc., is that they are known to be harmful to human and animal health. Similarly, UVGI uses UVC irradiation, a range of UV wavelengths that are known to be harmful to health. Thus, these technologies must be used with care, and their use is often limited due to such potential side effects.

Some specific drawbacks of HEPA (high-efficiency particulate air) filters are:

Mechanical filter only: no antimicrobial action or destruction of VOC molecules. As illustrated in FIG. 1, HEPA Filtration Mechanisms may include Diffusion between fibers of the HEPA, Interception by one or more HEPA fibers, Inertial Impaction to a HEPA fiber, and Electrostatic Attraction to a HEPA fiber.

FIG. 1 also illustrates that the Fractional Particle Collection Efficiency is greatly affected by which HEPA filtering mechanism regime the particle diameter falls into. Efficiency is compromised over a broad particle size range of ~0.015 μm-~2 μm; and is most difficult for particles in the size range 0.15-0.45 μm.

Prone to clogging, loss of efficiency with use.

Limited lifetime. Most are recommended to be changed every 6 months. Thus, efficacy often limited by lack of human discipline and financial reasons.

Expensive.

Discrete points of use/effectiveness. Filters are used at discrete locations in air-flow, and cannot thus trap microbes that are generated/enter the flow downstream.

Requires strong mechanical pumps to force air through them.

Cannot be used for water purification.

Trapping mechanisms have finite probabilities of emission.

The principal drawbacks of HEGA (high-efficiency gas adsorption) filters are:

Adsorption of gases only, effective against VOCs, but no antimicrobial action.

Not effective once its surface is saturated; HEGA needs to be regenerated by removal of adsorbed gas molecules from surface.

Cannot be used for water purification.

Some specific drawbacks of Ultraviolet Germicidal Irradiation (UVGI) are:

Direct exposure can be hazardous to humans.

Typically uses UVC (100 nm-280 nm wavelength range) light to kill or inactivate microbes. UVC radiation is hazardous to humans. Can only be used where humans are not exposed. Can only be used above human head-level ("upper room UVGI").

Normally not present in sunlight (absorbed by the atmospheric ozone layer).

Far UVC (200-235 nm wavelengths) is safer for humans due to lesser penetration depth in human tissue.

Indirect hazard creation by photolysis: generation of ozone and other harmful chemicals in room air.

Line-of-sight operation only.

Inconsistent effectiveness. Effectiveness depends on many factors, such as listed, and is thus hard to control consistently: Intensity of light; Duration of exposure; Reflectance and scattering of light from dust particles, affecting the light reaching the microorganism; Turbidity of the solvent (usually water); Lamp surface cleanliness.

Discrete application. Cannot shield against microorganisms introduced downstream.

Harmful to materials. UV-C breaks chemical bonds, thus ageing plastics, insulations, rubber, etc.

Cost is high.

Some specific drawbacks of Water Chlorination are:

Disinfection by-products such as trihalomethanes are hazardous to humans. Chronic exposure to trihalomethanes can cause cancer, heart disease, unconsciousness and even death.

Potential carcinogenicity requires regular monitoring of the concentration of harmful by-products in liquid (such as water).

Chlorination of swimming pool water causes eye irritation, skin irritation and adversely affects hair and teeth. Chronic exposure can likely lead to side-effects. Pools with too high of chlorine levels and built-up chloramines can also irritate the respiratory system.

Chlorine products are volatile and can vaporize from water and thus stop being effective against microbes. [Note: Bromine is less volatile than Chlorine (Cl2). Moreover, Bromine is less irritating than Cl2, but can also cause coughing, headaches and skin irritation. In addition, Bromine is more susceptible than Cl2 to UV degradation, and is harder to wash off the skin. Additionally, Bromine adversely affects taste and causes odor in drinking water applications.]

Not effective for air purification. And would be toxic.

Some specific drawbacks of state-of-the-art Photochemical Oxidation (PCO) filters are:

Typically uses titanium dioxide (TiO2) as the photo-activated antimicrobial material. (Photo-activated antimicrobial materials require exposure to UV light of certain wavelengths to display antimicrobial properties). Though TiO2 is the oldest known and most widely used material for photocatalytic oxidation/disinfection (PCO/PCD), it is not the most effective such material.

Not effective in the absence of UV light/in the dark.

Typically made by dispersing particles of TiO2 over a host surface, such as a fabric, a surface of a porous filter, or a solid surface such as an activated carbon filter. These fabrication processes result in a less-than-precise control of the effective surface area of the photocatalyst exposed to UV light. The total surface area and the surface area to volume ratio of the antimicrobial material are the most important morphological characteristics of the PCO material determining its disinfection efficacy. Thus, such products will not have the highest efficacies and may have significant part to part variation in the same. Such products will henceforth be referred to as "disordered structures" in this disclosure.

Discrete application. Cannot shield against microorganisms introduced downstream.

Thus, very few/if any of the state-of-the-art technologies prevent the growth of microbes or are designed for continuous antimicrobial action against existing microbes, both in terms of physical space as well as in terms of time length of action, and/or are designed to work without user/human intervention, and or do not pose any side-effect health-hazards. This teaching provides technologies, equipment, and methods which eliminates these disadvantages.

SUMMARY

In one aspect, a field-deployable antimicrobial assembly designed for gases or liquids, the assembly including: a substrate, a first material in contact with at least one surface of the substrate, where the first material includes nanotubes and/or nanopores; and a second material deposited on at least a portion of surfaces of the nanotubes and/or nanopores, where the second material includes at least one antimicrobial material.

In another aspect, a field-deployable antimicrobial assembly designed for gases or liquids, the assembly including: a substrate, a first material in contact with at least one surface of the substrate, where the first material includes nanotubes and/or nanopores; and a second material deposited on at least a portion of surfaces of the nanotubes and/or nanopores, where the second material includes at least one antimicrobial material, where the substrate includes a metal, and where the metal includes aluminum.

In another aspect, a field-deployable antimicrobial assembly designed for gases or liquids, the assembly including: a substrate, a first material in contact with at least one surface of the substrate, where the first material includes nanotubes and/or nanopores; and a second material deposited on at least a portion of surfaces of the nanotubes and/or nanopores, where the second material includes at least one antimicrobial material, where the second material is at least one of the following: copper, Cu; or silver, Ag; or titanium dioxide, $TiO2$ (doped or undoped); or titanium sub-oxides, $TiO(2-x)$, or zinc oxide, ZnO (doped or undoped); or tungsten oxide, $WO_3$; or tungsten sub-oxides, $WO(3-x)$.

In another aspect, a field-deployable antimicrobial assembly designed for gases or liquids, the assembly including: a substrate, a first material in contact with at least one surface of the substrate, where the first material includes nanotubes and/or nanopores; and a second material deposited on at least a portion of surfaces of the nanotubes and/or nanopores, where the second material includes at least one antimicrobial material, where the second material includes at least one composite film of antimicrobial semiconducting materials and antimicrobial metals.

In another aspect, a field-deployable antimicrobial assembly designed for gases or liquids, the assembly including: a substrate, a first material in contact with at least one surface of the substrate, where the first material includes nanotubes and/or nanopores, and where the first material includes at least one antimicrobial material; and a second material deposited on at least a portion of surfaces of the nanotubes and/or nanopores, where the second material includes at least one antimicrobial material.

In another aspect, a field-deployable antimicrobial assembly designed for gases or liquids, the assembly including: a substrate, a first material in contact with at least one surface of the substrate, where the first material includes nanotubes and/or nanopores, and where the first material includes at least one antimicrobial material; and a second material deposited on at least a portion of surfaces of the nanotubes and/or nanopores, where the second material includes at least one antimicrobial material, where the substrate includes a metal, and where the metal includes copper.

In another aspect, a field-deployable antimicrobial assembly designed for gases or liquids, the assembly including: a substrate, a first material in contact with at least one surface of the substrate, where the first material includes nanotubes and/or nanopores, and where the first material includes at least one antimicrobial material; and a second material deposited on at least a portion of surfaces of the nanotubes and/or nanopores, where the second material includes at least one antimicrobial material, where the second material is at least one of the following: copper, Cu; or silver, Ag; or titanium dioxide, $TiO2$ (doped or undoped); or titanium sub-oxides, $TiO(2-x)$, or zinc oxide, ZnO (doped or undoped); or tungsten oxide, $WO_3$; or tungsten sub-oxides, $WO(3-x)$.

In another aspect, a field-deployable antimicrobial assembly designed for gases or liquids, the assembly including: a substrate, a first material in contact with at least one surface of the substrate, where the first material includes nanotubes and/or nanopores, and where the first material includes at least one antimicrobial material; and a second material deposited on at least a portion of surfaces of the nanotubes and/or nanopores, where the second material includes at least one antimicrobial material, where the second material includes at least one composite film of antimicrobial semiconducting materials and antimicrobial metals.

In another aspect, a method of forming a high surface area antimicrobial material, the method including: providing a substrate; forming a first material on top of or within the substrate, where the first material is formed by solution-based coating, and where the first material includes nanotubes and/or nanopores; and forming a second material, where the second material is disposed on top of the first material, where the second material is formed by a vapor-phase coating process, and where the second material is antimicrobial.

In another aspect, a method of forming a high surface area antimicrobial material, the method including: providing a substrate; forming a first material on top of or within the substrate, where the first material is formed by solution-based coating, and where the first material includes nanotubes and/or nanopores; and forming a second material, where the second material is disposed on top of the first material, where the second material is formed by a vapor-phase coating process, and where the second material is antimicrobial, where the substrate compromises a metal, where the solution-based coating is anodization of the metal.

In another aspect, a method of forming a high surface area antimicrobial material, the method including: providing a substrate; forming a first material on top of or within the substrate, where the first material is formed by solution-based coating, and where the first material includes nanotubes and/or nanopores; and forming a second material, where the second material is disposed on top of the first material, where the second material is formed by a vapor-phase coating process, and where the second material is antimicrobial; and, an anneal, where the second material includes at least one composite film of antimicrobial semiconducting materials and antimicrobial metals, and where the anneal is performed after the second material is formed.

In another aspect, a method of forming a high surface area antimicrobial material, the method including: providing a substrate; forming a first material on top of or within the substrate, where the first material is formed by solution-based coating, and where the first material includes nanotubes and/or nanopores; and forming a second material, where the second material is disposed on top of the first material, where the second material is formed by a vapor-phase coating process, and where the second material is antimicrobial, where the second material is at least one of the following: copper, Cu; or silver, Ag; or titanium dioxide, $TiO2$ (doped or undoped); or titanium sub-oxides, $TiO(2-x)$, or zinc oxide, ZnO (doped or undoped); or tungsten oxide, $WO_3$; or tungsten sub-oxides, $WO(3-x)$.

BRIEF DESCRIPTION OF THE DRAWINGS

The present application can be best understood by reference to the following description taken in conjunction with the accompanying figures, in which like parts may be referred to by like numerals.

Figure 1:
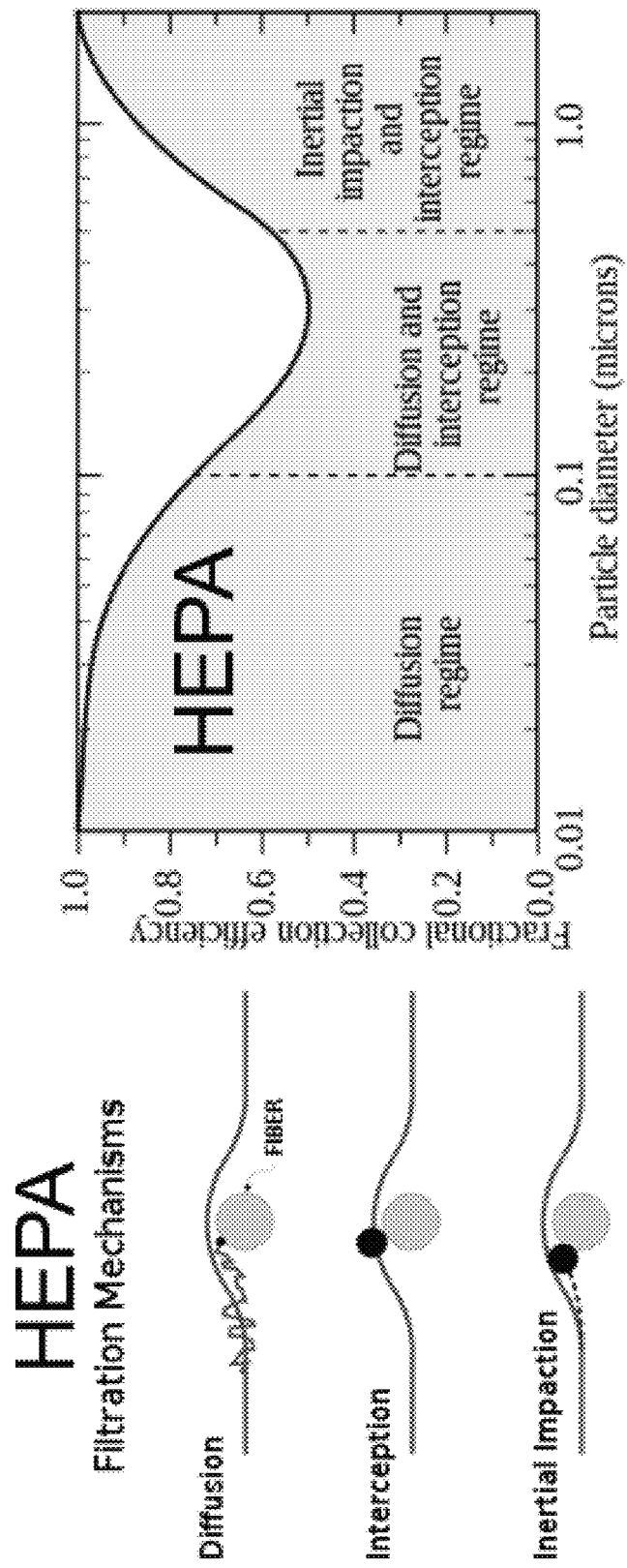
FIG. 1 illustrates HEPA Filtration Mechanisms and Fractional Particle Collection Efficiency affected by which HEPA filtering mechanism regime the particle diameter falls into.

The Figures described above are a representative set and are not exhaustive with respect to embodying the invention.

DETAILED DESCRIPTION

Disclosed are systems, devices, structures, methods, applications, and articles of manufacture for various series of industrial grade antimicrobial product designs, and materials and methods to make them highly effective products that offer continuous antimicrobial action, with a minimum of dependence on human discipline and skill once deployed, and with no harmful side-effects. Also disclosed are designs and methods of fabrication of field-deployable products for the inactivation of harmful microorganisms in air and liquid (such as water) and fluid more effectively than the current state-of-the-art technologies. Embodiments of this invention make use of antimicrobial materials, describing methods to fabricate and incorporate such materials onto surfaces, and methods to optimize the material fabrication processes to obtain highly reactive such antimicrobial surfaces. Described are advanced nanostructure fabrication methods of semiconducting and metallic materials that lead to an extremely high antimicrobial efficacy. Moreover, this disclosure teaches, describes, and suggests designs and other structural aspects of product assemblies incorporating such antimicrobial surfaces, the field-deployable nature of the product assemblies, as well as methods and embodiments to make them more effective. The following description is presented to enable a person of ordinary skill in the art to make and use the various embodiments. Descriptions of specific devices, techniques, and applications are provided only as examples. Various modifications to the examples described herein will be readily apparent to those of ordinary skill in the art, and the general principles defined herein may be applied to other examples and applications without departing from the spirit and scope of the various embodiments.

Reference throughout this specification to "one embodiment," "an embodiment," "one example," or similar language means that a particular feature, structure, or characteristic described in connection with the embodiment is included in at least one embodiment of the present invention. Thus, appearances of the phrases "in one embodiment," "in an embodiment," and similar language throughout this specification may, but do not necessarily, all refer to the same embodiment.

Furthermore, the described features, structures, or characteristics of the invention may be combined in any suitable manner in one or more embodiments. In the following description, numerous specific details are provided, such as examples of antimicrobial assemblies, antimicrobial tubes, antimicrobial coatings, antimicrobial material, fins and assemblies of fins, baffles and assemblies of baffles, HVAC ducting or liquid (such as water) pipes, semiconductor antimicrobial materials, antimicrobial efficacy, doping strategies, metallic antimicrobial materials, methods of coating, morphology/microstructure/nanostructure of coatings, post-coating annealing methods, compositions & nanostructures of antimicrobial coatings, programming, software modules, user selections, network transactions, database queries, database structures, hardware modules, hardware circuits, hardware chips, etc., to provide a thorough understanding of embodiments of the invention. One skilled in the relevant art can recognize, however, that the invention may be practiced without one or more of the specific details, or with other methods, components, materials, and so forth. In other instances, well-known structures, materials, or operations are not shown or described in detail to avoid obscuring aspects of the invention.

The schematic flow chart diagrams included herein are generally set forth as logical flow chart diagrams. As such, the depicted order and labeled steps are indicative of one embodiment of the presented method. Other steps and methods may be conceived that are equivalent in function, logic, or effect to one or more steps, or portions thereof, of the illustrated method. Additionally, the format and symbols employed are provided to explain the logical steps of the method and are understood not to limit the scope of the method. Although various arrow types and line types may be employed in the flow chart diagrams, they are understood not to limit the scope of the corresponding method. Indeed, some arrows or other connectors may be used to indicate only the logical flow of the method. For instance, an arrow may indicate a waiting or monitoring period of unspecified duration between enumerated steps of the depicted method. Additionally, the order in which a particular method occurs may or may not strictly adhere to the order of the corresponding steps shown.

Example Product, Field-Deployable Antimicrobial Assemblies

It is noted that the following example embodiments discuss field-deployable antimicrobial assemblies by way of example. However, other field-deployable antimicrobial assemblies or methods can be utilized in other example embodiments.

Figure 2A:
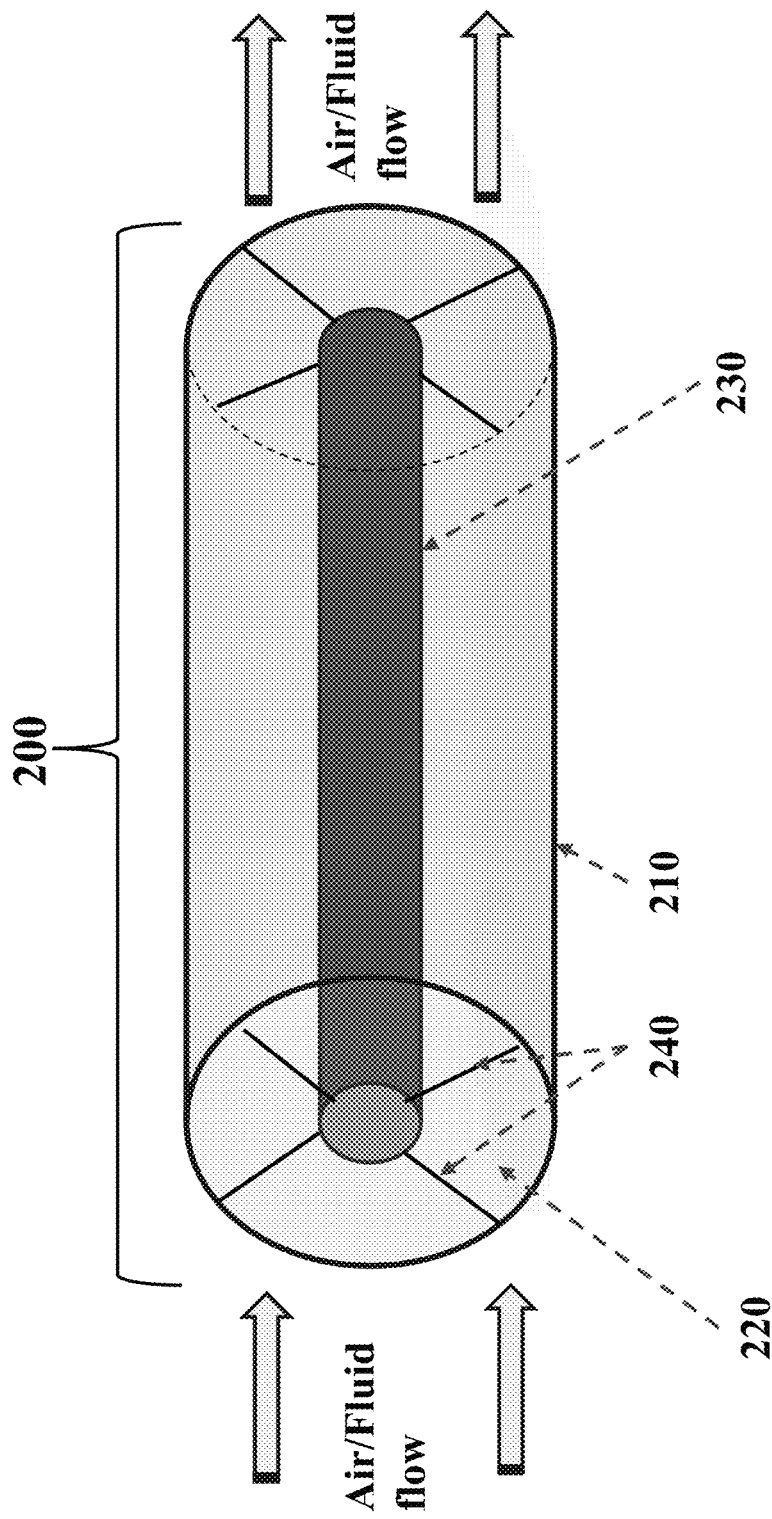
FIG. 2A illustrates an example schematic of a first field-deployable antimicrobial assembly, according to some embodiments.

As illustrated in FIG. 2A an exemplary schematic of a field-deployable antimicrobial assembly is presented. Field-deployable antimicrobial assembly 200 may include Antimicrobial (AM) tube 210, Inner surface of AM tube 210 coated with antimicrobial material 220, UV/Vis lamps in inner tube 230, and struts 240. Antimicrobial (AM) tube 210 may be concentric tubes in shape, although a square or rectangular cross-sectional shape is possible, but this may result in non-uniform light distribution and reflection/absorption. A gang of concentric tubes may be encased by a cross-sectional 'box' shape; at least the interior surface of the cross-sectional 'box' shape may be 'active' with respect to antimicrobial activity, for example, also coated with antimicrobial material. Antimicrobial (AM) tube 210, the 'outer tube' in FIG. 2A, has an antimicrobial coating, the details of which will be described later herein. UV/Vis lamps in inner tube 230 supplies the light to assist the desired antimicrobial activity, the details of which are described later herein and may include a UV/Vis lamp assembly. UV lamp assemblies may be formed with UV LEDs to provide advantages such as much lower power costs as well as longer 'lamp' life of the UV LEDs, and thus lower maintenance. As well, heat/thermal design is less critical and costly with the LED variants, as LEDs run at lower temperatures and generate less heat than conventional UV lamps. UV LEDs are available in the UVA wavelengths, 395 nm and 365 nm, and can be used in place of any of the lamp assemblies/light sources referenced herein.

The tubular shapes assure circumferentially uniform intensity of light output from inner tube 230, and circumferentially uniform intensity of light incident on interior of the walls/antimicrobial coating of antimicrobial (AM) tube 210.

Antimicrobial (AM) tube 210 may have lengths ranging from approx. 1 ft. (0.3 m) to approx. 6.5 ft. (2 m), and diameters ranging from approx. 1 ft. (0.3 m) to 6.5 ft. (2 m), depending on the application and engineering considerations. The UV/Vis lamps in inner tube 230 may be attached to outer antimicrobial (AM) tube 210 by means of struts 240 as illustrated in FIG. 2A.

Multiple such assemblies, such as field-deployable antimicrobial assembly 200, can be joined lengthwise by flanges and/or other physical attachment devices/mechanisms thus obtaining continuous pipes, thus providing continuous antimicrobial surfaces.

Inner tube 230 may include a UV light which may have the requirement of UVA (wavelength range 315 nm-400 nm), and preferably not UVC, but possible. Technically UVC will also work. However, it is generally avoided due to the health hazard issue. It also might require the products to go through additional regulatory clearances, which increase time to market.

UVA is not harmful to humans, unlike UVC (harmful). UVA is plentiful in sunshine. Depending on the specific antimicrobial material used in the coating of the interior of outer antimicrobial (AM) tube 210, visible light (>400 nm, up to ~720 nm) can also be used, and artificial lighting can also be eliminated in some embodiments.

Electrical power will be required for UV/Vis lamps. The access for electrical power to the UV/Vis lamps of inner tube 230 may utilize struts 240 to minimize the impact on the efficient travel of the air or liquid (such as water) or fluid flowing thru the field-deployable antimicrobial assembly 200. As well as maximizing the energy efficiency of the assembly with respect to the overall deployed system.

Figure 2B:
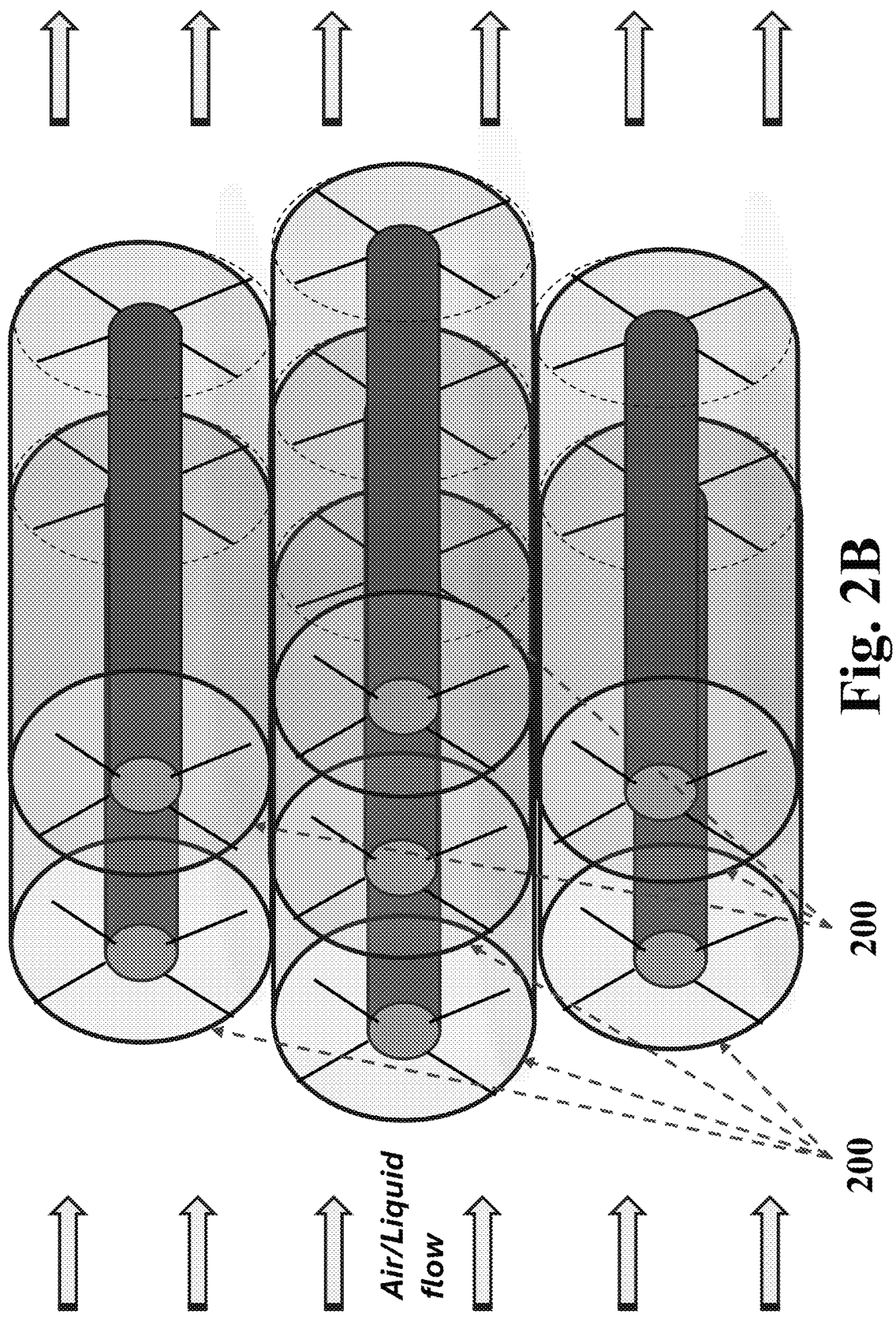
FIG. 2B illustrates an example schematic of a gang of field-deployable antimicrobial assembly, according to some embodiments.

As illustrated in FIG. 2B, several antimicrobial (AM) tubes, for example, antimicrobial assembly 200 (an exemplary seven are shown), can be ganged to form a master-assembly. The antimicrobial assembly 200 may also be 'daisy-chained' when a multiplicity of field-deployable antimicrobial assembly 200s (or 700s, 600s, 500s, 400s, or 300s, etc.) are collected/configured into a group or cluster. The assembly of FIG. 2A, and subsequent embodiments in FIGS. 2-7, can be ganged with other assemblies to create master-assemblies that further increase the total antimicrobial surface area of a product.

Figure 3:
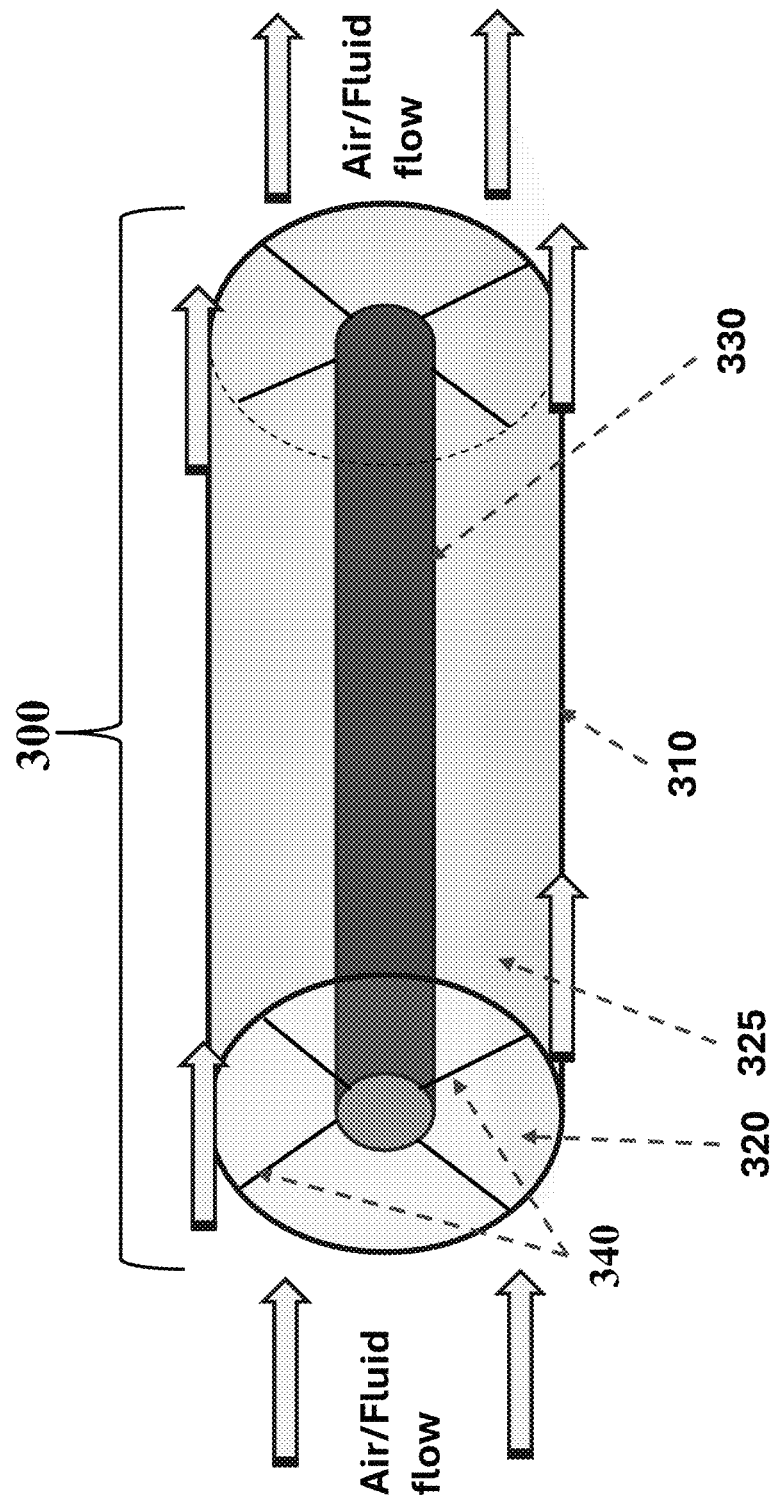
FIG. 3 illustrates an example schematic of a second field-deployable antimicrobial assembly, according to some embodiments.

As illustrated in FIG. 3 an exemplary schematic of a second field-deployable antimicrobial assembly is presented. Second field-deployable antimicrobial assembly 300 may include Antimicrobial (AM) tube 310, Inner surface of AM tube 310 coated with transmissive antimicrobial material 320, Outer surface of AM tube 310 coated with antimicrobial material 325, UV/Vis lamps in inner tube 330, and struts 340.

Antimicrobial (AM) tube 310 may be concentric tubes in shape, although a square or rectangular cross-sectional shape is possible. However, this may result in non-uniform light distribution and reflection/absorption. A gang of concentric tubes may be encased by a cross-sectional 'box' shape; at least the interior surface of the cross-sectional 'box' shape may be 'active' with respect to antimicrobial activity, for example, also coated with antimicrobial material.

Antimicrobial (AM) tube 310, the 'outer tube' in FIG. 3, has an antimicrobial coating on both the interior 320 and exterior 325 of the AM tube 310, the details of which will be described later herein. UV/Vis lamps in inner tube 330 may supply the light to assist the desired antimicrobial activity, the details of which are described later herein and may include a UV/Vis lamp assembly.

The tubular shapes assure circumferentially uniform intensity of light output from inner tube 330, and circumferentially uniform intensity of light incident on interior/exterior of at least the walls/antimicrobial coating of antimicrobial (AM) tube 310 and thus on the exterior located antimicrobial material 325.

Antimicrobial (AM) tube 310 may have lengths ranging from approx. 1 ft. (0.3 m) to approx. 6.5 ft. (2 m), and diameters ranging from approx. 1 ft. (0.3 m) to 6.5 ft. (2 m), depending on the application and engineering considerations. The UV/Vis lamps in inner tube 330 may be attached to outer antimicrobial (AM) tube 310 by means of struts 340 as illustrated in FIG. 3.

Multiple such assemblies, such as second field-deployable antimicrobial assembly 300, can be joined lengthwise by flanges and/or other physical attachment devices/mechanisms thus obtaining continuous pipes, accordingly providing continuous antimicrobial surfaces.

Inner tube 330 may include a UV light which may have the requirement of UVA (wavelength range 315 nm-400 nm), and preferably not UVC, but possible. Technically UVC will also work. However, it is generally avoided due to the health hazard issue. It also might require the products to go through additional regulatory clearances, which increase time to market.

UVA is not harmful to humans, unlike UVC (harmful). UVA is plentiful in sunshine. Depending on the specific antimicrobial material used in the coating of the interior of outer antimicrobial (AM) tube 310, visible light (>400 nm, up to ~720 nm) can also be used, and artificial lighting can also be eliminated in some embodiments.

Second field-deployable antimicrobial assembly 300 may have both the interior surface 320 of AM tube 310 and the exterior surface 325 of AM tube 310 coated with an antimicrobial coating. This may require that the material of AM tube 310 and the antimicrobial material 320 coated on the interior surface of AM tube 310 to be transparent or nearly transparent to the wavelength(s) spectrum of the specific UV/Vis light of inner tube 330. The transmisiveness of antimicrobial material 325 disposed on the exterior of AM tube 310 may be designed depending on engineering and efficacy considerations. For example, if second assembly 300 is ganged laterally, one may design antimicrobial material 325 to be at least partially transmissive so that adjacent second field-deployable antimicrobial assembly 300s may benefit.

Electrical power will be required to energize and operate UV/Vis lamps employed in/as inner tube 330. The routing access for electrical power to the UV/Vis lamps of inner tube 330 may utilize struts 340 to minimize the impact on the efficient travel of the air or liquid (such as water) or fluid flowing thru the field-deployable antimicrobial assembly 300. Additionally, this configuration maximizes the energy efficiency of the assembly with respect to the overall deployed system. With proper isolative material choices and construction to prevent electrical shorts, struts 340 may be constructed, at least partially, of electrically conductive material, thus eliminating any wiring or cords supplying power to the UV/Vis lamps of 330. The antimicrobial assembly 300 may also be 'daisy-chained' when a multiplicity of field-deployable antimicrobial assembly 300s (or 700s, 600s, 500s, 400s, or 200s, etc.) are collected/configured into a group or cluster.

This embodiment will approximately double the surface area of antimicrobial coating per antimicrobial assembly 300.

Figure 4:
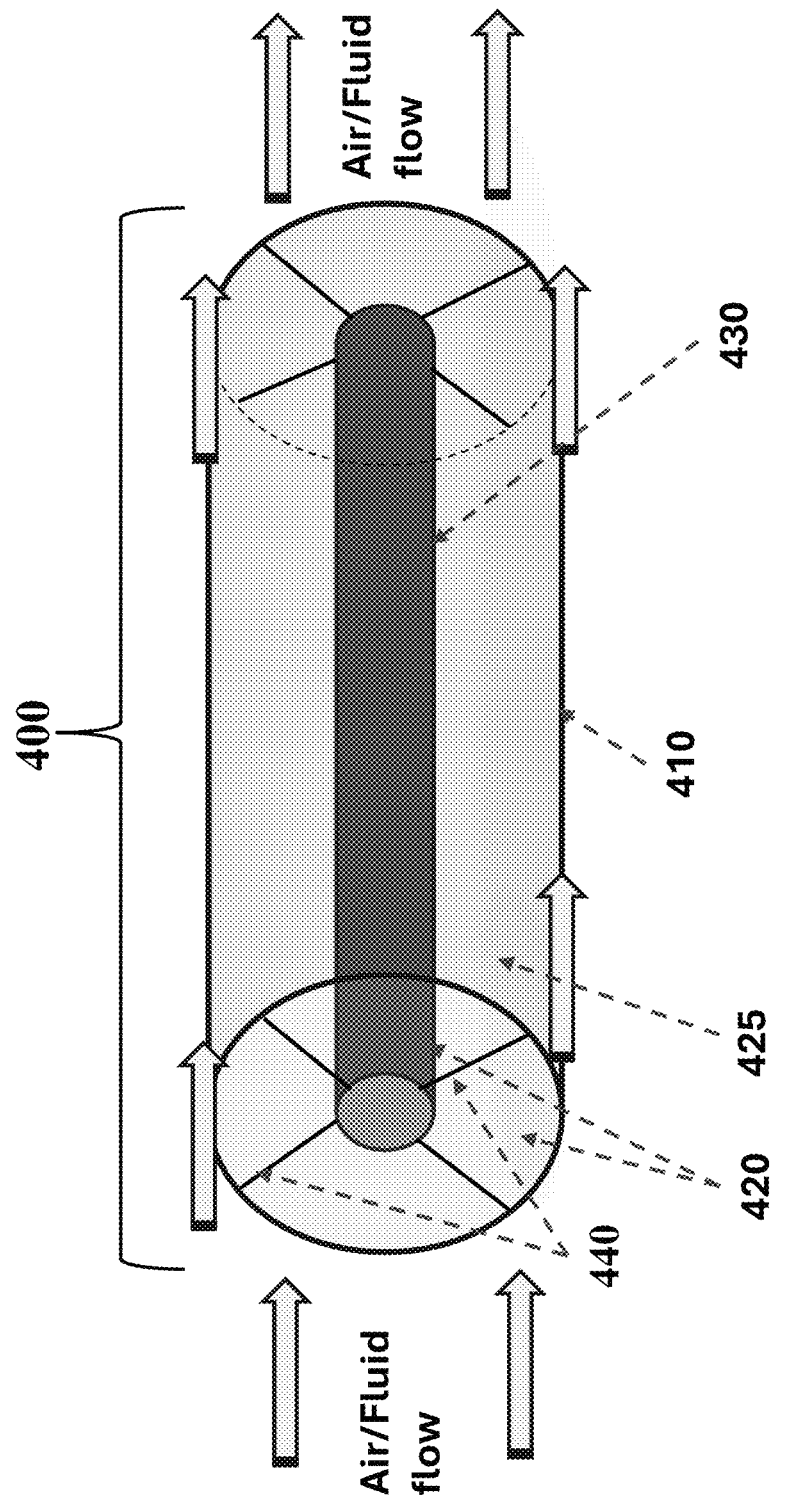
FIG. 4 illustrates an example schematic of a third field-deployable antimicrobial assembly, according to some embodiments.

As illustrated in FIG. 4 an exemplary schematic of a third field-deployable antimicrobial assembly is presented. Third field-deployable antimicrobial assembly 400 may include Antimicrobial (AM) tube 410, Inner surface of AM tube 410 coated with transmissive antimicrobial material 420, Outer surface of AM tube 410 coated with antimicrobial material 425, UV/Vis lamps in inner tube 430 coated with transmissive antimicrobial material 420, and struts 440.

Antimicrobial (AM) tube 410 may be concentric tubes in shape, although a square or rectangular cross-sectional shape is possible. However, this may result in non-uniform light distribution and reflection/absorption. A gang of concentric tubes may be encased by a cross-sectional 'box' shape; at least the interior surface of the cross-sectional 'box' shape may be 'active' with respect to antimicrobial activity, for example, also coated with antimicrobial material.

Antimicrobial (AM) tube 410, the 'outer tube' in FIG. 4, has both a transmissive antimicrobial coating on its interior surfaces and antimicrobial material 425 coated on its exterior, the details of which will be described later herein. UV/Vis lamps in inner tube 430 coated with transmissive antimicrobial material 420 supplies the light to assist the desired antimicrobial activity, the details of which are described later herein and may include a UV/Vis lamp assembly.

The tubular shapes assure circumferentially uniform intensity of light output from inner tube 430 coated with transmissive antimicrobial material 420, and circumferentially uniform intensity of light incident on the interior of the walls/transmissive antimicrobial material 420 coating of antimicrobial (AM) tube 410 and thus on the exterior located antimicrobial material 425.

Antimicrobial (AM) tube 410 may have lengths ranging from approx. 1 ft. (0.3 m) to approx. 6.5 ft. (2 m), and diameters ranging from approx. 1 ft. (0.3 m) to 6.5 ft. (2 m), depending on the application and engineering considerations. The UV/Vis lamps in inner tube 430 may be attached to outer antimicrobial (AM) tube 410 by means of struts 440 as illustrated in FIG. 4.

Multiple such assemblies, such as third field-deployable antimicrobial assembly 400, can be joined lengthwise by flanges and/or other physical attachment devices/mechanisms thus obtaining continuous pipes, accordingly providing continuous antimicrobial surfaces.

Inner tube 430 may include a UV light which may have the requirement of UVA (wavelength range 315 nm-400 nm), and preferably not UVC, but possible. Technically UVC will also work. However, it is generally avoided due to the health hazard issue. It also might require the products to go through additional regulatory clearances, which increases time to market. UVA is not harmful to humans, unlike UVC (harmful). UVA is plentiful in sunshine. Depending on the specific antimicrobial material used in the coating of the inner tube 430 transmissive microbial material 420 and the interior of outer antimicrobial (AM) tube 410, visible light (>400 nm, up to ~720 nm) can also be used, and artificial lighting can also be eliminated in some embodiments.

Third field-deployable antimicrobial assembly 400 may have both the interior surface of AM tube 410 and the exterior surface of AM tube 410 coated with an antimicrobial coating. This may require that the material of at least the AM tube 410 and the antimicrobial material coated on the interior surface of AM tube 410 and the exterior surface of inner tube 430 to be transparent or nearly transparent to the chosen wavelength(s) spectrum of the specific UV/Vis light of inner tube 430. The antimicrobial material 425 on the exterior of outer AM tube 410 may be designed to be very absorptive if this increases its antimicrobial properties, or may not be. If the antimicrobial material 425 on the exterior of outer AM tube 410 is chosen to be transmissive, this may aid activation of antimicrobial material in an adjacent AM tube, when in a ganged configuration. It is a matter of engineering, efficiency, and types of anti-microbial material chosen at a specific surface within the assembly/system whether a specific antimicrobial material is transparent, partially transmissive, or opaque to the electromagnetic (EM) spectrum generated by the UV/Vis (or other EM source) lamp employed in inner tube 430.

Electrical power will be required to energize and operate UV/Vis lamps employed in/as inner tube 430. The routing access for electrical power to the UV/Vis lamps of inner tube 430 may utilize struts 440 so to minimize the impact on the efficient travel of the air or liquid (such as water) or fluid flowing thru the third field-deployable antimicrobial assembly 400. Additionally, this configuration maximizes the energy efficiency of the assembly with respect to the overall deployed system. With proper electrically isolative material choices and construction to prevent electrical shorts, struts 440 may be constructed, at least partially, of electrically conductive material, replacing any wiring or cords to supply electricity to the UV/Vis lights, thus eliminating any wiring or cords supplying power to the UV/Vis lamps of 430. The antimicrobial assembly 400 may also be 'daisy-chained' when a multiplicity of third field-deployable antimicrobial assembly 400s (or 700s, 600s, 500s, 300s, or 200s, etc.) are collected/configured into a group or cluster.

This embodiment will more than double the surface area of antimicrobial coating per antimicrobial assembly 400.

Figure 5:
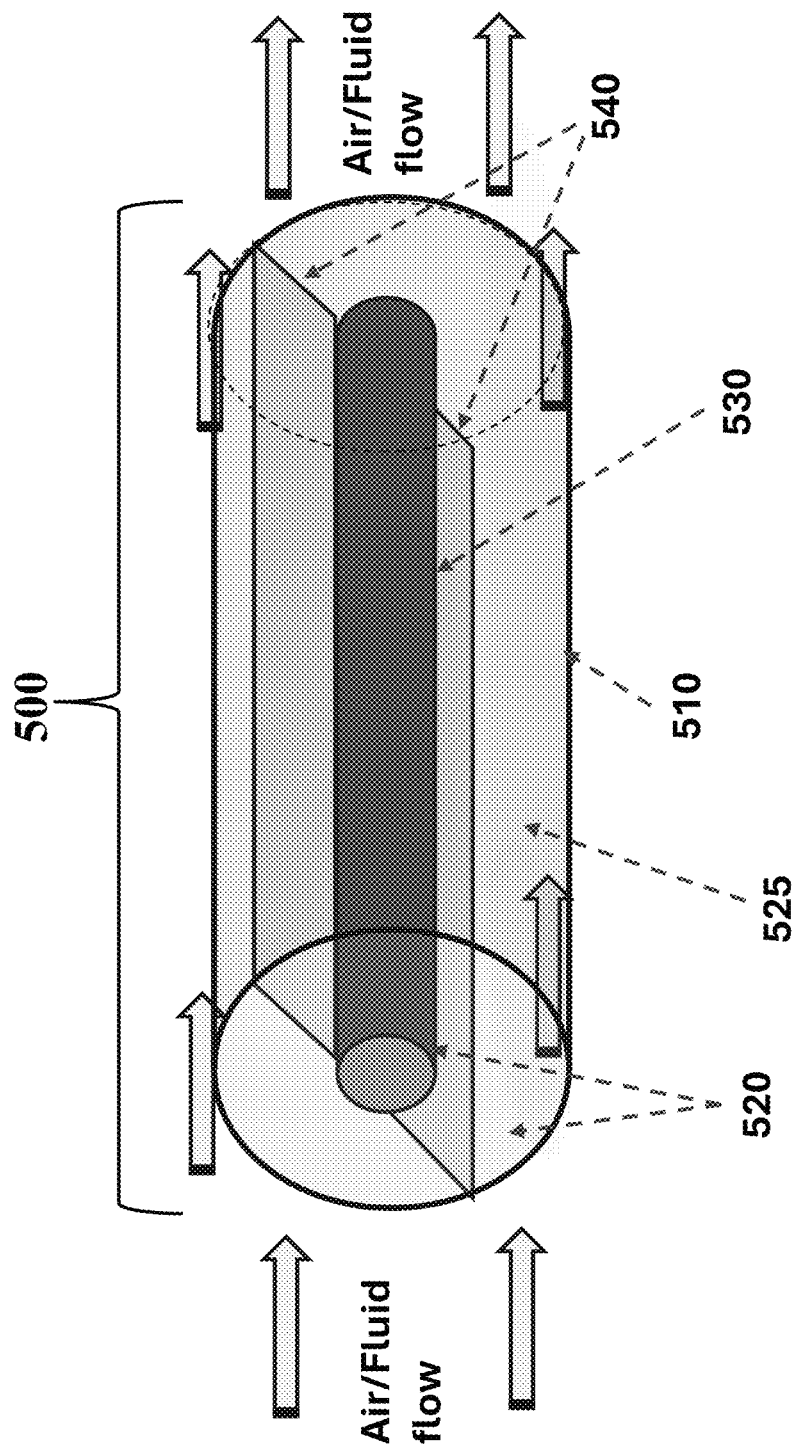
FIG. 5 illustrates an example schematic of a fourth field-deployable antimicrobial assembly, according to some embodiments.

As illustrated in FIG. 5 an exemplary schematic of a fourth field-deployable antimicrobial assembly is presented. Fourth field-deployable antimicrobial assembly 500 may include Antimicrobial (AM) tube 510, Inner surface of AM tube 510 coated with transmissive antimicrobial material 520, Outer surface of AM tube 510 coated with antimicrobial material 525, UV/Vis lamps in inner tube 530 coated with transmissive antimicrobial material 520, and fins 540, which may be coated with transmissive antimicrobial material 520 and/or antimicrobial material 525 depending on engineering considerations. Although FIG. 5 illustrates two fins 540, one may greatly increase the area of exposed antimicrobial material (to the passing air or liquid or fluid) by increasing the number of fins 540. The number of fins 540 within each fourth field-deployable antimicrobial assembly 500 may include about 2 fins 540, about 4 fins 540, about 6 fins 540, about 8 fins 540, about 10 fins 540, about 12 fins 540, and so on; which may be expressed by #fins 540=2n or 2n+1, where n is a positive integer. The limitation on the number to fins 540 may be determined by engineering, physics, and cost considerations such as space and cross-sectional area coverage of open and closed to the path of the Air/Liquid flow.

Antimicrobial (AM) tube 510 may be concentric tubes in shape, although a square or rectangular cross sectional shape is possible. However, this may result in non-uniform light distribution and reflection/absorption. A gang of concentric tubes may be encased by a cross-sectional 'box' shape; at least the interior surface of the cross-sectional 'box' shape may be 'active' with respect to antimicrobial activity, for example, also coated with antimicrobial material.

Antimicrobial (AM) tube 510, the 'outer tube' in FIG. 5, has both a transmissive antimicrobial coating 520 on its interior surfaces and antimicrobial material 525 coated on its exterior, the details of which will be described later herein. UV/Vis lamps in inner tube 530 may be coated with transmissive antimicrobial material 520 and supplies the light to assist the desired antimicrobial activity, the details of which are described later herein and may include a UV/Vis lamp assembly.

The tubular shapes assure circumferentially uniform intensity of light output from inner tube 530 coated with transmissive antimicrobial material 520, and circumferentially uniform intensity of light incident on the interior of the walls/transmissive antimicrobial material 520 coating of antimicrobial (AM) tube 510 and thus on the exterior located antimicrobial material 525. The intensity of light incident on the fins 540 will vary with radial distance from the inner tube/UV lamp 530, but will generally not be lower than the light intensity on the inner/outer surfaces of the outer tube-inner surface of AM tube 510 coated with transmissive antimicrobial material 520 and outer surface of AM tube 510

Antimicrobial (AM) tube 510 may have lengths ranging from approx. 1 ft. (0.3 m) to approx. 6.5 ft. (2 m), and diameters ranging from approx. 1 ft. (0.3 m) to 6.5 ft. (2 m), depending on the application and engineering considerations. The UV/Vis lamps in inner tube 530 may be attached to outer antimicrobial (AM) tube 510 by means of fins 540 as illustrated in FIG. 5, although this may not be the only structure connecting inner tube 530 to outer AM tube 510. For example, some or all of fins 540 may not extend from inner tube 530 to AM tube 510, or vice versa, and struts or some other structure may hold the tubes (AM 510 & inner 530) in place and touch. These can be determined by engineering analysis of flow and microbial kill efficacy for various configurations.

Multiple such assemblies, such as fourth field-deployable antimicrobial assembly 500, can be joined lengthwise by flanges and/or other physical attachment devices/mechanisms thus obtaining continuous pipes, accordingly providing continuous antimicrobial surfaces.

Inner tube 530 may include a UV light which may have the requirement of UVA (wavelength range 315 nm-400 nm), and preferably not UVC, but possible. Technically UVC will also work. However, it is generally avoided due to the health hazard issue. It also might require the products to go through additional regulatory clearances, which increases time to market. UVA is not harmful to humans, unlike UVC (harmful). UVA is not harmful to humans, unlike UVC (harmful). UVA is plentiful in sunshine. Depending on the specific antimicrobial material used in the coating of the inner tube 530 transmissive microbial material 520 and the interior of outer antimicrobial (AM) tube 510, visible light (>400 nm, up to ~720 nm) can also be used, and artificial lighting can also be eliminated in some embodiments.

Fourth field-deployable antimicrobial assembly 500 may have both the interior surface of AM tube 510 and the exterior surface of AM tube 510 coated with an antimicrobial coating. This may require that the material of at least the AM tube 510 and the antimicrobial material coated on the interior surface of AM tube 510 and the exterior surface of inner tube 530 to be transparent or nearly transparent to the chosen wavelength(s) spectrum of the specific UV/Vis light of inner tube 530. The antimicrobial material 525 on the exterior of outer AM tube 510 may be designed to be very absorptive if this increases its antimicrobial properties, or may not be. If the antimicrobial material 525 on the exterior of outer AM tube 510 is chosen to be transmissive, this may aid activation of antimicrobial material in an adjacent AM tube, when in a ganged configuration. It is a matter of engineering, efficiency, and types of anti-microbial material chosen at a specific surface within the assembly/system whether a specific antimicrobial material is transparent, partially transmissive, or opaque to the electromagnetic (EM) spectrum generated by the UV/Vis (or other EM source) lamp employed in inner tube 530. For example, the material of outer tube AM tube 510, or some portion of the cross-section of AM tube 510, may be chosen to be reflective so that the UV/Vis light may be reflected back into the antimicrobial coatings 520 and 525, thereby increasing their antimicrobial activity.

Electrical power may be required to energize and operate UV/Vis lamps employed in/as inner tube 530. The routing access for electrical power to the UV/Vis lamps of inner tube 530 may utilize fins 540 so to minimize the impact on the efficient travel of the air or liquid (such as water) or fluid flowing thru the fourth field-deployable antimicrobial assembly 500. Additionally, this configuration maximizes the energy efficiency of the assembly with respect to the overall deployed system. With proper electrically isolative material choices and construction to prevent electrical shorts, fins 540 may be constructed, at least partially, of electrically conductive material, replacing any wiring or cords to supply electricity to the UV/Vis lights, thus eliminating any wiring or cords supplying power to the UV/Vis lamps of inner tube 530. The antimicrobial assembly 500 may also be 'daisy-chained' when a multiplicity of fourth field-deployable antimicrobial assembly 500s (or 700s, 600s, 400s, 300s, or 200s, etc.) are collected/configured into a group or cluster.

This embodiment will dramatically increase the surface area of antimicrobial coating per antimicrobial assembly 500. Moreover, the presence of fins 540 may slow down the Air/Fluid flow to ensure more microorganisms contact antimicrobial surfaces (increase the probability of microorganisms landing on/contacting antimicrobial surfaces), generally due to increased adhesion of Air/Fluid molecules to the antimicrobial surfaces and/or crowding of the air/fluid flow molecules. This embodiment can be used to increase the antimicrobial surface area by very large factors. Each fin will increase the area by (Length of fin 540×(Inner-radius of outer AM tube 510–Outer-radius of inner tube 530)×N) where N is the number of fins 540.

Figure 6:
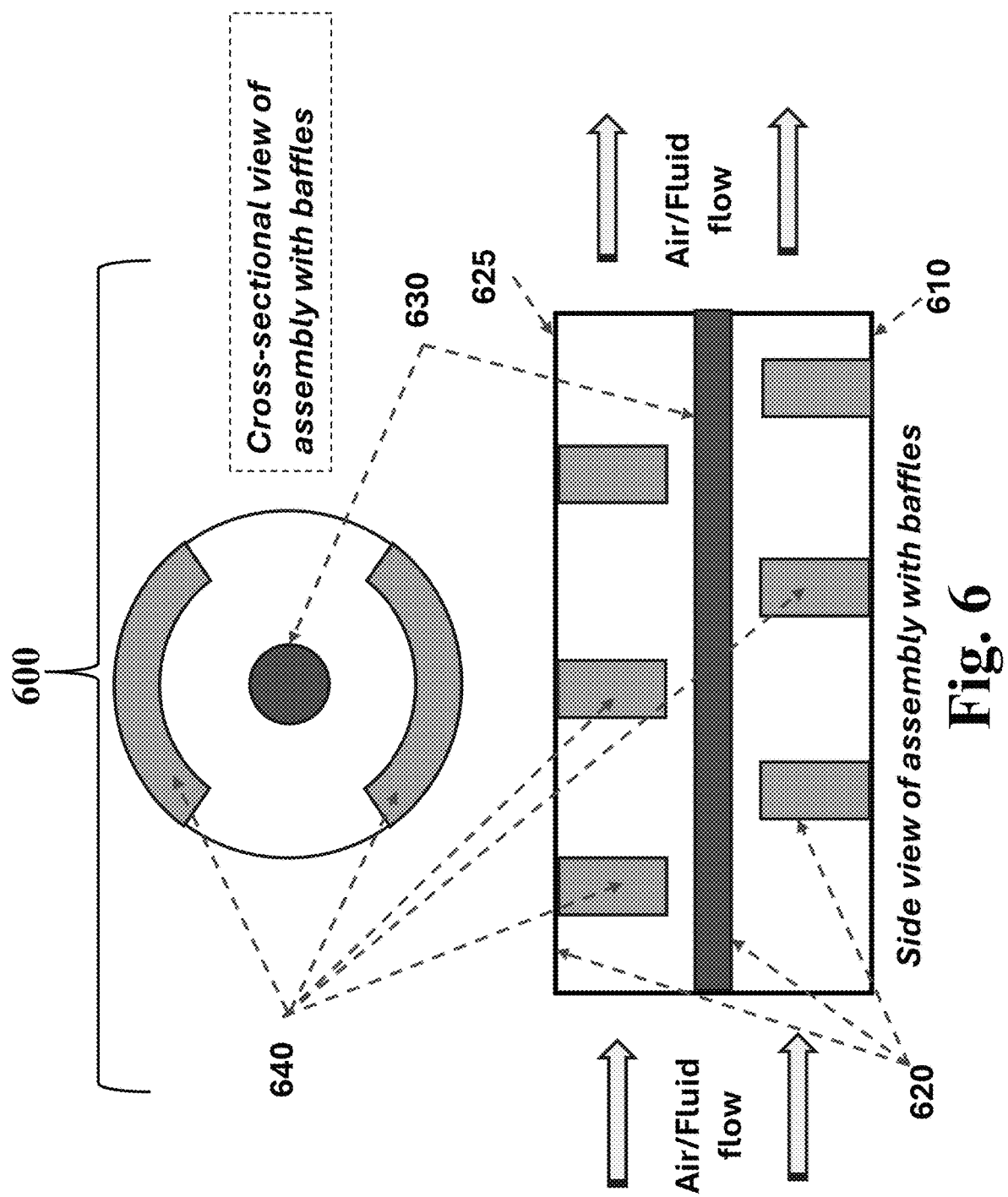
FIG. 6 illustrates an example schematic of a fifth field-deployable antimicrobial assembly, according to some embodiments.

As illustrated in FIG. 6 an exemplary schematic of a fifth field-deployable antimicrobial assembly is presented. Fifth field-deployable antimicrobial assembly 600 may include Antimicrobial (AM) tube 610, Inner surface of AM tube 610 coated with transmissive antimicrobial material 620, Outer surface of AM tube 610 coated with antimicrobial material 625, UV/Vis lamps in inner tube 630 coated with transmissive antimicrobial material 620, and baffles 640, which may be coated with transmissive antimicrobial material 620 and/or antimicrobial material 625 depending on engineering considerations.

Although FIG. 6 illustrates six baffles 640, one may greatly increase the area of exposed antimicrobial material (to the passing air or liquid or fluid) by increasing the number of baffles 640 and the shape therein. The number of baffles 640 within each fifth field-deployable antimicrobial assembly 600 may include about 2 baffles 640, about 4 baffles 640, about 6 baffles 640, about 8 baffles 640, about 10 baffles 640, about 12 baffles 640, and so on; which may be expressed by #baffles 640=2n or 2n+1, where n is a positive integer. This may total between 2 and 100 or more depending on at least engineering considerations and the length of fifth field-deployable antimicrobial assembly 600. The limitation on the number to baffles 640 may be determined by engineering, physics, and cost considerations such as space and cross-sectional area coverage of open and closed to the path of the Air/Liquid flow.

Baffles 640 could cover a portion of the perimeter (as shown in FIG. 6) or the entire perimeter of the tube. Baffles could have heights ranging from 0.2× of the inner diameter of fifth field-deployable antimicrobial assembly 600 to 0.5×. Baffles 640 may be perforated when designed thin, and may include thru tubes if thick enough, thereby increasing antimicrobial exposed surface area and lowering the delta pressure inlet to outlet. The presence of Baffles 640 impedes the air/fluid flow, thus increasing the probability of microorganisms landing on antimicrobial surfaces but will generally increase the delta pressure inlet to outlet and potentially cost energy to push the air/fluid thru the assembly 600. The intensity of the light, which may be produced by UV/Vis lamps within 630, impinging on baffles 640 will vary with radius, but will be consistent along the length of the Antimicrobial (AM) tube 610 (for each radial position), and will never be lower than the intensity on the inner surface of outer tube Antimicrobial (AM) tube 610 in this specific configuration.

Antimicrobial (AM) tube 610 may be concentric tubes in shape, although a square or rectangular cross-sectional shape is possible. However, this may result in non-uniform light distribution and reflection/absorption. A gang of concentric tubes may be encased by a cross-sectional 'box' shape; at least the interior surface of the cross-sectional 'box' shape may be 'active' with respect to antimicrobial activity, for example, also coated with antimicrobial material.

Antimicrobial (AM) tube 610, the 'outer tube' in FIG. 6, has both a transmissive antimicrobial coating 620 on its interior surfaces and antimicrobial material 625 coated on its exterior, the details of which will be described later herein. UV/Vis lamps in inner tube 630 may be coated with transmissive antimicrobial material 620 and supplies the light to assist the desired antimicrobial activity, the details of which are described later herein and may include a UV/Vis lamp assembly.

The tubular shapes assure circumferentially uniform intensity of light output from inner tube 630 coated with transmissive antimicrobial material 560, and circumferentially uniform intensity of light incident on the interior of the walls/transmissive antimicrobial material 620 coating of antimicrobial (AM) tube 610 and thus on the exterior located antimicrobial material 625.

Antimicrobial (AM) tube 610 may have lengths ranging from approx. 1 ft. (0.3 m) to approx. 6.5 ft. (2 m), and diameters ranging from approx. 1 ft. (0.3 m) to 6.5 ft. (2 m), depending on the application and engineering considerations. The UV/Vis lamps in inner tube 630 may be attached to outer antimicrobial (AM) tube 610 by means of fins or struts as illustrated in at least FIGS. 2-5 herein, although this may not be the only structure connecting inner tube 630 to outer AM tube 610. For example, some, most or all of baffles 640 may not extend from inner tube 630 to AM tube 610, or vice versa, and struts or some other structure may hold the tubes (AM 610 & inner 630) in place and touch. These can be determined by engineering analysis of flow and microbial kill efficacy for various configurations.

Multiple such assemblies, such as fifth field-deployable antimicrobial assembly 600, can be joined lengthwise by flanges and/or other physical attachment devices/mechanisms thus obtaining continuous pipes, accordingly providing continuous antimicrobial surfaces.

Inner tube 630 may include a UV light which may have the requirement of UVA (wavelength range 315 nm-400 nm), and preferably not UVC, but possible. Technically UVC will also work. However, it is generally avoided due to the health hazard issue. It also might require the products to go through additional regulatory clearances, which increases time to market. UVA is not harmful to humans, unlike UVC (harmful). UVA is not harmful to humans, unlike UVC (harmful). UVA is plentiful in sunshine. Depending on the specific antimicrobial material used in the coating of the inner tube 630 transmissive microbial material 620 and the interior of outer antimicrobial (AM) tube 610, visible light (>400 nm, up to ~720 nm) can also be used, and artificial lighting can also be eliminated in some embodiments.

Fifth field-deployable antimicrobial assembly 600 may have both the interior surface of AM tube 610 and the exterior surface of AM tube 610 coated with an antimicrobial coating. This may require that the material of at least the AM tube 610 and the antimicrobial material coated on the interior surface of AM tube 610 and the exterior surface of inner tube 630 to be transparent or nearly transparent to the chosen wavelength(s) spectrum of the specific UV/Vis light of inner tube 630. The antimicrobial material 625 disposed on the exterior of outer AM tube 610 may be designed to be very absorptive if this increases its antimicrobial properties, or may not be. If the antimicrobial material 625 on the exterior of outer AM tube 610 is chosen to be transmissive, this may aid activation of antimicrobial material in an adjacent AM tube, when in a ganged configuration. It is a matter of engineering, efficiency, and types of anti-microbial material chosen at a specific surface within the assembly/system whether a specific antimicrobial material is transparent, partially transmissive, or opaque to the electromagnetic (EM) spectrum generated by the UV/Vis (or other EM source) lamp employed in inner tube 630. For example, the material of outer tube AM tube 610, or some portion of the cross-section of AM tube 610, may be chosen to be reflective so that the UV/Vis light may be reflected back into the antimicrobial coatings 620 and 625, thereby increasing their antimicrobial activity.

Electrical power may be required to energize and operate UV/Vis lamps employed in/as inner tube 630. The routing access for electrical power to the UV/Vis lamps of inner tube 630 may utilize baffles 640 so to minimize the impact on the efficient travel of the air or liquid (such as water) or fluid flowing thru the fifth field-deployable antimicrobial assembly 600. Additionally, this configuration maximizes the energy efficiency of the assembly with respect to the overall deployed system. With proper electrically isolative material choices and construction to prevent electrical shorts, a few of the baffles 640 may be constructed, at least partially, of electrically conductive material, replacing any wiring or cords to supply electricity to the UV/Vis lights, thus eliminating any wiring or cords supplying power to the UV/Vis lamps of inner tube 630. The antimicrobial assembly 600 may also be 'daisy-chained' when a multiplicity of fifth field-deployable antimicrobial assembly 600s (or 700s, 500s, 400s, 300s, or 200s, etc.) are collected/configured into a group or cluster.

This embodiment will dramatically increase the surface area of antimicrobial coating per antimicrobial assembly 600. Moreover, the presence of baffles 640 may slow down the Air/Fluid flow to ensure more microorganisms contact antimicrobial surfaces (increase the probability of microorganisms landing on/contacting antimicrobial surfaces), generally due to increased adhesion of Air/Fluid molecules to the antimicrobial surfaces and/or crowding of the air/fluid flow molecules. This embodiment can be used to [a] increase the antimicrobial surface area by very large factors, and [b] modulate the flow rate of the air/fluid through the tube to optimize antimicrobial efficacy.

Figure 7:
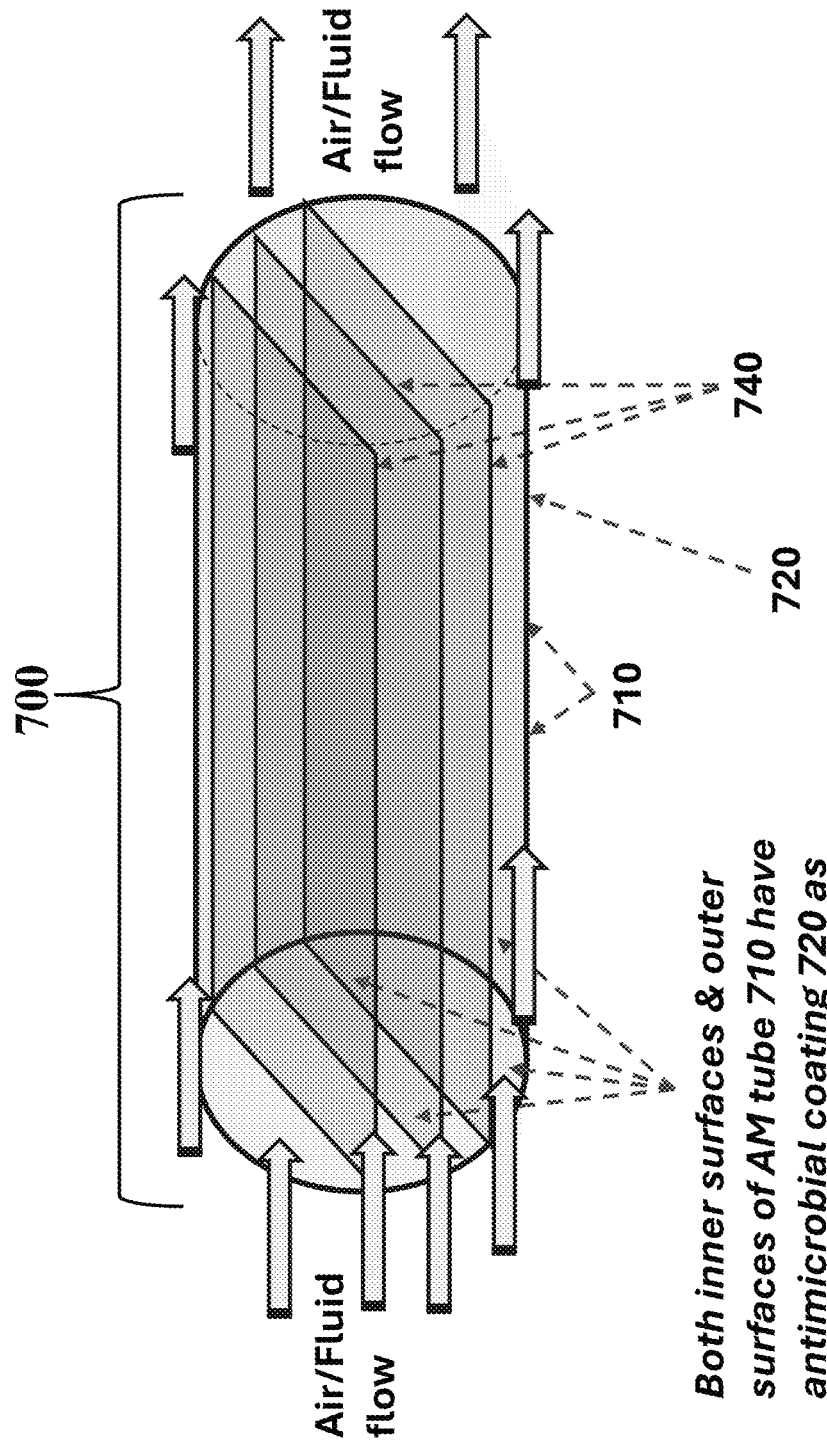
FIG. 7 illustrates an example schematic of a sixth field-deployable antimicrobial assembly, according to some embodiments.

As illustrated in FIG. 7 an exemplary schematic of a sixth field-deployable antimicrobial assembly is presented. Sixth field-deployable antimicrobial assembly 700 may include Antimicrobial (AM) tube 710, Visible light transmissive antimicrobial material 720, and Fins or fins with baffles 740, which may be coated with transmissive antimicrobial material 720. This embodiment has no artificial UV lighting. Antimicrobial material 720 coating may be designed to work without the need for artificial lighting and may be at least partially transmissive to that light as well, depending on engineering considerations.

Although FIG. 7 illustrates three fins or fins with baffles 740, one may greatly increase the area of exposed antimicrobial material (to the passing air or liquid or fluid) by increasing the number of fins or fins with baffles 740 and the shape therein. The number of fins or fins with baffles 740 within each sixth field-deployable antimicrobial assembly 700 may include about 2 fins or fins with baffles 740, about 4 fins or fins with baffles 740, about 6 fins or fins with baffles 740, about 8 fins or fins with baffles 740, about 10 fins or fins with baffles 740, about 12 fins or fins with baffles 740, and so on; which may be expressed by #fins or fins with baffles 740=2n or 2n+1, where n is a positive integer. This may total between 2 and 100 or more depending on at least engineering considerations and the length of sixth field-deployable antimicrobial assembly 700. The limitation on the number to fins or fins with baffles 740 may be determined by engineering, physics, and cost considerations such as space and cross-sectional area coverage of open and closed to the path of the Air/Liquid flow.

Fins or fins with baffles 740 may be perforated when designed thin, and may include thru tubes if thick enough, thereby increasing antimicrobial exposed surface area and lowering the delta pressure inlet to outlet. The presence of Fins or fins with baffles 740 impedes the air/fluid flow, thus increasing the probability of microorganisms landing on antimicrobial surfaces but will generally increase the delta pressure inlet to outlet and potentially cost energy to push the air/fluid thru the assembly 700. This embodiment will allow usage in dark environments, allow usage in environments where there is adequate natural light, and will not need any electrical power to operate.

Antimicrobial (AM) tube 710 may be concentric tubes in shape, although a square or rectangular cross sectional shape is possible. However, this may result in a less uniform light distribution and reflection/absorption. A gang of concentric tubes may be encased by a cross-sectional 'box' shape; at least the interior surface of the cross-sectional 'box' shape may be 'active' with respect to antimicrobial activity, for example, also coated with antimicrobial material.

Antimicrobial (AM) tube 710 includes a transmissive or at least partially transmissive antimicrobial coating 720 on its interior surfaces and exterior surfaces, the details of which will be described later herein. The material which the Fins or fins with baffles 740 may be transmissive or at least partially transmissive. The transmissive or partially transmissive material for either or both the AM Tube 710 composition and the antimicrobial coating 720 may be designed to permit natural light transmission. The transmissive or partially transmissive material of antimicrobial coating 720 may be designed to be effective with no light activation, thus being able to effectively provide antimicrobial efficacy in dark environments, the details of which are described later herein.

The shapes of the components within antimicrobial assembly 700, which may include Antimicrobial (AM) tube 710, antimicrobial material 720, and Fins or fins with baffles 740, may be designed to assure uniform intensity of any ambient/natural light impingement upon any antimicrobial coating therein. As well, shapes of the components within antimicrobial assembly 700, which may include Antimicrobial (AM) tube 710, antimicrobial material 720, and Fins or fins with baffles 740, may be designed to maximize the flow of air/fluid thru antimicrobial assembly 700, commonly indicated by a minimum (drop) difference between the inlet pressure and the outlet pressure.

Antimicrobial (AM) tube 710 may have lengths ranging from approx. 1 ft. (0.3 m) to approx. 6.5 ft. (2 m), and diameters ranging from approx. 1 ft. (0.3 m) to 6.5 ft. (2 m), depending on the application and engineering considerations. Being no lamps in this embodiment, there is no need to route electrical wiring as well as any locking of air/fluid flow from UV/Vis lamps.

Multiple such assemblies, such as sixth field-deployable antimicrobial assembly 700, can be joined lengthwise by flanges and/or other physical attachment devices/mechanisms thus obtaining continuous pipes, accordingly providing continuous antimicrobial surfaces.

Sixth field-deployable antimicrobial assembly 700 may have both the interior surface of AM tube 710 and the exterior surface of AM tube 710 coated with antimicrobial coating 720. Many or all surfaces of the Fins or fins with baffles 740 may be coated with antimicrobial coating 720. It is a matter of engineering, efficiency, and types of antimicrobial material chosen at a specific surface within the assembly/system whether a specific antimicrobial material is transparent, partially transmissive, or opaque to the electromagnetic (EM) spectrum environment antimicrobial assembly 700 may be placed in.

The antimicrobial assembly 700 may also be 'daisychained' when a multiplicity of sixth field-deployable antimicrobial assembly 700s (or 600s, 500s, 400s, 300s, or 200s, etc.) are collected/configured into a group or cluster.

This embodiment will dramatically increase the surface area of antimicrobial coating per antimicrobial assembly 700. Moreover, the presence of fins or fins with baffles 740 may slow down the Air/Fluid flow to ensure more microorganisms contact antimicrobial surfaces (increase the probability of microorganisms landing on/contacting antimicrobial surfaces), generally due to increased adhesion of Air/Fluid molecules to the antimicrobial surfaces and/or crowding of the air/fluid flow molecules. This embodiment can be used to increase the antimicrobial surface area by very large factors. This embodiment can be used to [a] increase the antimicrobial surface area by very large factors, and [b] modulate the flow rate of the air/fluid through the tube to optimize antimicrobial efficacy with no electric usage or lamps to maintain.

Figure 8:
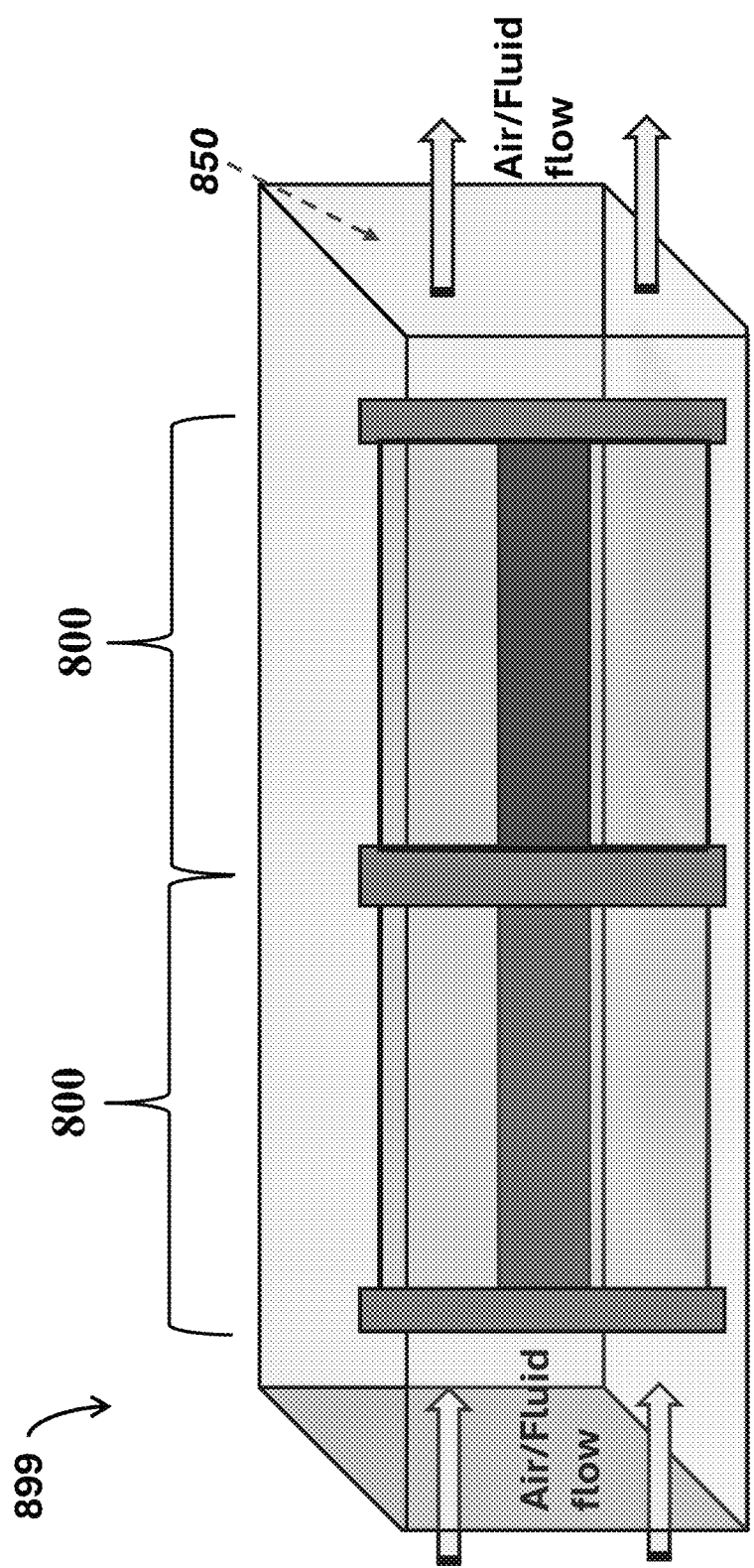
FIG. 8 illustrates an example schematic of field-deployable antimicrobial assemblies deployed in an exemplary HVAC or water pipe application/product, according to some embodiments.

As illustrated in FIG. 8 an exemplary schematic of field-deployable antimicrobial assemblies 800 deployed in an exemplary HVAC or water pipe application/product 899 is presented. For example, field-deployable antimicrobial assembly 800 may be disposed within HVAC air ducting or water pipes 850 or in any other suitable containment scheme wherein the air/fluid of interest may be forced to come into contact with the anti-microbial material included within field-deployable antimicrobial assembly 800. Field-deployable antimicrobial assembly 800 may include at least any of the components described herein as well as combinations not shown of embodiments and elements of the embodiments.

Field-deployable antimicrobial assemblies 800 can be deployed in HVAC ducting or in water pipes, generally aligned with the direction of the air/fluid flow. Depending on engineering goals, calculations, and considerations, field-deployable antimicrobial assemblies 800 may cover only a portion of the cross-section of ducting/pipes within 850, or can cover the entire cross-section (sizing of assembly can be customized to the size of the duct/pipe).

Although FIG. 8 illustrates two, individual field-deployable antimicrobial assemblies 800 can be joined by means of flanges (grey rectangles in FIG. 8) to create a continuous/nearly infinitely long pipe-like assembly. Field-deployable antimicrobial assemblies 800 may also be deployed in places where the desired air/fluid is static (no forced convection), e.g., as in water storage tanks, water reservoirs, etc.

Furthermore, natural (or deliberate) convection may facilitate circulate air/fluid through field-deployable antimicrobial assemblies 800. In such a deployment the system may rely on natural convection to circulate air/fluid through field-deployable antimicrobial assemblies 800 and make microbes incident on the antimicrobial coatings. Proper deployment of 800 and 899 (as well as the other antimicrobial assemblies and systems described herein) may eliminate harmful microbes & VOCs, and additionally can prevent the growth of microbes.

Detailed Description: Materials Used to Fabricate Antimicrobial Coating(s) Described in at Least Herein The materials which may be used to fabricate the antimicrobial coatings as taught, described, and suggested in at least herein, are detailed in the next section. For example, some of the antimicrobial materials/coatings described herein may include the following reference numbers: 220, 320, 325, 420, 425, 520, 525, 620, 625, and 720.

Semiconductor antimicrobial materials include Titanium dioxide ($TiO_2$) and its sub-oxides ($TiO_{(2-x)}$, TiO, and $Ti_2O$), Tungsten oxide ($WO_3$) and its sub-oxide ($WO_{(3-x)}$, Zinc oxide (ZnO) and its sub-oxide $ZnO_{(1-x)}$, Iron (III) oxide ($Fe_2O_3$) and its sub-oxide $Fe_2O_{(3-x)}$, Copper (I) oxide ($Cu_2O$) and its sub-oxide ($Cu_2O_{(1-x)}$), Antimony oxide ($Sb_2O_3$) and its sub-oxide ($Sb_2O_{(3-x)}$), Bismuth oxide ($Bi_2O_3$) and its sub-oxide ($Bi_2O_{(3-x)}$), Cadmium sulfide (CdS), Tin sulfide ($SnS_2$), Bismuth sulfide ($Bi_2S_3$), Silver bromide (AgBr), Silver iodide (AgI), Bismuth Oxy-Iodide (BiOI), Nickel tungsten oxide ($NiWO_4$) and its sub-oxide ($NiWO_{(4+x)}$), Bismuth tungsten oxide ($Bi_2WO_6$) and its sub-oxide ($Bi_2WO_{(6-x)}$), Carbon nitride ($C_3N_4$), Silver phosphate ($Ag_3PO_4$), Bismuth vanadium oxide ($BiVO_4$) and its sub-oxide ($BiVO_{(4+x)}$, Zinc indium sulfide ($ZnIn_2S_4$), and the like, which may be classified as photocatalytic semiconductors.

These materials are classified as photocatalytic semiconductors, i.e., they need to be excited by light of appropriate energy to become reactive and display photochemical oxidation/disinfection (PCO/PCD) properties. Depending on the semiconductor antimicrobial material used, the energy/wavelength threshold of excitation can vary from the UVA to the visible range. This range spans wavelengths from approximately 380 nm to approximately 600 nm. The two most common antimicrobial semiconductors are $TiO_2$ and ZnO; these two however require light of wavelength smaller than 387 nm to display antimicrobial activity.

Semiconductor antimicrobial materials can be activated by either UVA light (315 nm-400 nm) or Visible light (400 nm-700 nm). As mentioned earlier, UVGI technologies in contrast need to use UVC light, which has a much lower wavelength range (100 nm-280 nm), with UVC wavelengths having the disadvantage of being harmful to health. However, UVA and Visible light have no known harmful health effects and have been safely employed in various applications with decades of safe use.

Doped semiconductor antimicrobial materials are another class of materials which may be utilized for effective antimicrobial activity. The antimicrobial efficacy of semiconductor materials depends on the wavelength/energy range of incident light and the energy band gap of the semiconductor. The incident light needs to have adequate energy to excite electrons from the valence band of the semiconductor to the conduction band, i.e., photoactivation occurs only if the incident light energy is equal to or greater than the energy band gap of the semiconductor.

The energy and wavelength of light are related by the equation Energy hcl, where h is the Planck's constant, c is the speed of light and/is the wavelength of light. As mentioned before, most common photocatalytic semiconductors are generally sensitive to light in the UVA range (wavelengths 315 nm to 400 nm). This is particularly true for Titanium dioxide ($TiO_2$) and Zinc oxide (ZnO), the two most common semiconductor photocatalyst materials. $TiO_2$ has an energy band gap of approx. 3 electron-volts to approx. 3.2 electron-volts (e.v.) depending on the crystal structure, and thus needs light of wavelength equal to or smaller than approx. 387 nm. Similarly, ZnO has an energy band gap of approx. 3.2 e.v., and thus also needs light of wavelengths equal to or smaller than approx. 387 nm to display photocatalytic activity, and thus antimicrobial effects.

The solar spectrum reaching earth spans a broad wavelength range with the peak intensity around 500 nm, and the approximate range of high intensity lies between 360 nm-700 nm. Thus, UVA is present in the solar spectrum, but the overlap is only over a small range of approx. 360 nm-400 nm. Accordingly, in most actual use situations, artificial UVA lighting is required to obtain significant antimicrobial efficacy from semiconductor materials in their pure chemical state. However, if the energy band gap of the semiconductor can be reduced by the addition of dopants (excitation wavelength increased), then they would display enhanced efficacy in natural sunlight conditions without the need for artificial UVA lighting.

Several distinctly different doping strategies can be used to reduce the band gap of semiconductors.

Doping with transition elements with partially-filled d-orbitals: examples of transition elements include Nickel, Molybdenum, Tantalum, Vanadium, Chromium, Ruthenium, and the like.

Doping with rare earth elements, i.e., elements from the Lanthanide and Actinide series, result in defect energy levels in the band gap, thus reducing the effective energy band gap. Examples of such elements include Lanthanum, Yttrium, Ytterbium, Erbium, Dysprosium, Gadolinium, Samarium, Europium, Cerium, and the like.

Doping with noble metal nanoparticles: noble metal nanoparticles can absorb light and generate hot electrons, which effectively reduce the band gap energy of the semiconductor. Examples of such dopants can be Silver, Gold, Copper, Platinum, and Palladium.

Doping with non-metallic elements such as, for example, Nitrogen, Sulfur, Carbon, and Phosphorus, which also reduces the energy band gap of the semiconductors.

Metallic antimicrobial materials can also provide antimicrobial activity. Certain pure metals, for example, such as Copper (Cu) and Silver (Ag) and certain alloys of Copper and Silver, are known to be antimicrobial. Copper alloys with Copper content >58 weight % up to 100 weight % are antimicrobial. This includes alloys such as Copper-Zinc alloys (Brasses), Copper-Tin alloys (Bronzes), Copper-Nickel alloys, Copper-Zinc-Nickel alloys (also known as "nickel silvers"), Cu-Tin alloys, Cu—Al—Ni alloys, Cu—Si alloys and others, as long as the Copper content in the alloy is in the range mentioned earlier. The US Environmental Protection Agency (US EPA) recognizes >500 different Copper alloys as antimicrobial.

Detailed Description: Methods of Coating Antimicrobial Materials and Methods to Optimize the Coatings Methods of coating antimicrobial materials on the assemblies & methods to optimize the morphology/microstructure/nanostructure of such coatings (post-coating processing) to maximize antimicrobial efficacy are taught, described, and suggested in at least herein, and are detailed in the next section. For example, some of the antimicrobial assemblies on which the antimicrobial materials may be coated as described herein may include at least the following reference numbers: 200, 300, 400, 500, 600, and 700. For example, some of the antimicrobial materials/coatings described herein may include the following reference numbers: 220, 320, 325, 420, 425, 520, 525, 620, 625, and 720.

The product assembly embodiments described in this disclosure may be coated using conformal (non-line-of-sight) coating methods, as the product assembly embodiments may include of curved and complex surfaces and many of the embodiments may require coating of all sides/faces of the structures. If instead, line of sight methods are used, the assemblies must then be composed of many smaller parts which would have to be fit together after coating to form the assemblies. This would make the manufacturing process needlessly complicated and expensive and might also compromise their robustness and reliability in the field.

Use of some of the conformal coating methods described herein also offer a host of options to engineer the morphology and nanostructure of the coatings to obtain super high surface areas and surface area/volume ratios of antimicrobial materials, which in turn will result in super high antimicrobial efficacy.

Solution-phase conformal coating methods: Solution-phase conformal coating methods may include Electrochemical techniques such as Electrodeposition/Electroplating and Anodization, Electroless Deposition techniques, and Dip Coating techniques. In general, not all materials can be deposited using any of the techniques mentioned. For example, usually Electroplating only works for depositing metals (not oxides), As well, Anodization generally works primarily for depositing oxides (not metals).

Electrodeposition/Electroplating: Electrodeposition/Electroplating are techniques where the part-to-be-coated is made the cathode in an electrochemical cell. The coating material is either made the anode or is dissolved in an electrolyte/medium. Upon the application of electrical energy (current/voltage) of the correct polarity and strength, the coating material deposits on the surface of the part to be coated (cathode). Due to fundamental scientific reasons, this technique [a] requires the surface of the part-to-be-coated to be electrically conductive, and [b] these techniques generally only work for metals and metallic alloys, not for the direct deposition of semiconductors.

In at least one embodiment, Copper antimicrobial metal or Silver antimicrobial metal can be deposited using this technique on antimicrobial assemblies where the outer tube, fins, and/or baffles (as well as any other desired surface in the antimicrobial assembly) are formed from an electrically conductive material, for example, such as stainless steel, galvanized steel, galvanized iron, or aluminum.

Anodization: Anodization is a technique which results in the formation of an oxide of a metal on the surface of the metal (self-oxide). In this method, the metal-part-to-be-oxidized may be made the anode in an electrochemical cell, and the electrolyte chemistry and electrical power (current, voltage) conditions may be chosen to produce an oxidation reaction on the surface of the metal, thus converting the surface layers to the oxide of the exposed metal, the metal-oxide (self-oxide). Thus, anodization can be used to form/coat the surface of a metal with its self-oxide. Due to fundamental scientific reasons, anodization cannot be used to deposit metals.

In one embodiment, titanium dioxide can thus be formed on the surface of the outer tube, fins, and baffles (as well as any other desired surface in the antimicrobial assembly), if they are made from titanium metal. In another embodiment, where the outer tube, fins and baffles (as well as any other desired surface in the antimicrobial assembly) are made from galvanized steel or galvanized iron, Zinc oxide (ZnO) can be formed on the surface by anodization ("galvanization" is the process of coating zinc on iron/steel, i.e., galvanized iron/steel materials are already coated with zinc metal). In another embodiment, where the outer tube, inner tube, fins and baffles (as well as any other desired structures in the antimicrobial assembly) are made from transparent and electrically non-conductive glass or plastic materials, a first coating of a metal such as Zinc or Titanium can be applied using techniques such as Electrodeposition, Dip coating, or Vapor Phase Coating (described later), and then followed by anodization to create a second coating of antimicrobial titanium oxide or zinc oxide on the surfaces of the outer tube, inner tube, fins and baffles, and any other desired surface.

Electroless Deposition/Plating: Electroless Deposition/Plating is a solution-based coating technique where metals and metallic alloys can be deposited on the surfaces of electrically conductive or electrically non-conductive materials. The mechanism is "autocatalytic" in nature, where both the source material of the coating and the reducing agent are incorporated in the same solvent bath. The reducing agent reduces the metallic source material by a process known as "electron exchange", which then results in the deposition of the source material on surfaces immersed in the solvent. The solution bath may also contain other chemicals that may act as buffers, stabilizers, and complexing agents.

In one embodiment, Copper or Silver antimicrobial metal can be coated directly on the surfaces of the inner tube, outer tube, fins and baffles (as well as any other desired surface in the antimicrobial assembly) using Electroless deposition. In another embodiment, a first coating could apply metals such as Titanium or Zinc on the surfaces using Electroless deposition, and a second coating would then use Anodization to create, for example, antimicrobial Titanium oxide or Zinc oxide.

Dip coating: Dip coating is a technique where the part/structure to be coated is dipped in a liquid in which the material-to-be-coated is present either as a suspension or as a melt. When the part/structure is withdrawn from the liquid, its surface is coated with the liquid. If the liquid is a solvent with the material-to-be-coated present as a suspension, then a drying step may be required to remove/vaporize the solvent, leaving behind a surface coated with the particles of the suspension. If the liquid is a melt, then the liquid coating solidifies to a solid coating upon cooling.

In one embodiment, the surfaces of the anti-microbial assembly can be dip coated with molten zinc. In this embodiment, any assembly material which can survive the temperature of molten zinc, approx. 450° C., can be used. In another embodiment, the surfaces of the assembly can be coated with Titanium dioxide or Zinc oxide nanoparticles suspended in an appropriate solvent (e.g., water).

Vapor Phase Conformal Coating Methods: Vapor phase conformal (non-line-of-sight) coating methods may include Atomic Layer Deposition (ALD), Plasma-enhanced Atomic Layer Deposition (PE-ALD), Plasma-assisted Atomic Layer Deposition (PA-ALD), Chemical Vapor Deposition (CVD), Plasma-Enhanced and Plasma-Assisted Chemical Vapor Deposition (PE-CVD, PA-CVD), Metal-organic Chemical Vapor Deposition (MOCVD), Atomic Vapor Deposition (AVD), and the like.

The above techniques involve placing the part-of-be-coated, for example, the surface of the outer tube, fins, and baffles (as well as any other desired surface in the antimicrobial assembly) into a chamber or chambers where atmosphere and temperature may be controlled. Coating may be achieved by pumping in "precursor" gases, i.e., gases containing the elements to be coated, into the chamber, allowing the precursor gases to react with the surface of the part or with each other, thus forming the coating, and removal of unreacted precursors and reaction by-products from the chamber. The part is typically heated to enable the reaction (s). Precursor gases are typically pre-heated before they enter the chamber to facilitate the chemical reactions. The flow rates of precursor gases, carrier and purge gases, as well as the pressure in the chamber, are also controlled to achieve desired quality and growth rate of the coatings. Plasma-enhanced/plasma-assisted processes utilize plasmas of one or more precursors, inert gases, and reactant gases to enable lower temperature reactions and thus reduce the temperature requirement to which the part and precursors must be heated.

ALD (Atomic Layer Deposition) is the most conformal deposition technique known today and is the only technique currently that can be used in advanced semiconductor chip manufacturing which require 100% or close-to-100% coating conformality on ultra-small 3D nanoscale structures that additionally may have ultra-high aspect ratios. ALD offers true-atomic scale control of material composition. ALD can used to coat metallic, semiconducting and insulating materials, for example, the surface of the outer tube, fins, and baffles (as well as any other desired surface in the antimicrobial assembly) as described herein. ALD and CVD are very versatile techniques that can be used to coat most any of the semiconducting and metallic antimicrobial materials included in this disclosure.

ALD generally requires that precursor gases react with the surface of the part to be coated; for example, the surface of the outer tube, fins, and baffles (as well as any other desired surface in the antimicrobial assembly) as described herein. Accordingly, in ALD processes, precursors and reactant gases are introduced into the chamber sequentially. A first pulse sends in a first precursor (e.g., a metal precursor). Once the first precursor has completed its reaction with the surface, a second pulse sends in an inert gas (e.g., Argon) that purges the chamber of unreacted first precursor and by-products from the first reaction. If, for example, the material being coated is a two-component compound, e.g., Titanium dioxide ($TiO_2$) or Zinc oxide (ZnO), a third pulse sends in the second precursor (e.g., Oxygen precursor such as $H_2O$ or Ozone), followed by a fourth pulse that sends in inert gas again to remove unreacted second precursor and by-products from the chamber. The coating proceeds in this sequential manner until the desired thickness is achieved. In ALD processes, precursor gases are typically pre-heated to temperatures 60° C.-200° C. before they enter the chamber. Parts-to-be-coated are typically heated to temperatures of 80° C.-650° C.

CVD processes, on the other hand, generally proceed wherein substantially all requisite precursor and reactant gases are pumped in simultaneously. Gas concentrations and flow rates are controlled in appropriate proportions to form coatings of the desired composition. Gases mix and react with each other in the chamber and coatings form on the surface of the part, for example, the surface of the outer tube, fins, and baffles (as well as any other desired surface in the antimicrobial assembly) as described herein. Gases are usually pre-heated to a temperature between 60° C.-200° C. before entering the chamber. The part is typically heated to a temperature of 80° C.-800° C., as appropriate for the chemical reaction and the coating quality, to enable the reactions to happen close to or on the surface of the part. Gases are continuously pumped in and out of the chamber to ensure uniform coating composition with time and constant coating rates.

PE-CVD and PA-CVD utilize plasmas of reactant gases and inert, generally Noble gases, to enable lower reaction temperatures. Thus PE-CVD and PA-CVD coatings can typically be done at temperatures much lower than CVD coatings of the same materials.

MOCVD is a type of CVD that uses metal-organic precursors (e.g., trimethyl-aluminum, tri-methyl gallium, etc.).

AVD is a blend of ALD and CVD, wherein one of the precursor gases is fed in continuously (such as CVD), while the other precursor(s) are fed in sequentially (such as ALD). AVD offers many of the benefits of ALD, while achieving coating rates approaching CVD.

Embodiments using conformal vapor phase coating methods: In one embodiment, antimicrobial semiconductors, for example, such as $TiO_2$, ZnO, $WO_3$, and others, can be coated directly on the antimicrobial assembly desired surfaces using any of the above-mentioned conformal vapor phase coating methods. In another embodiment, antimicrobial metals such as Copper or Silver can be coated directly on the antimicrobial assembly using the same methods.

In another embodiment, composite films of antimicrobial semiconducting materials and antimicrobial metals can be coated directly on the antimicrobial assembly using the above methods. This embodiment allows the formation of a vast range of complex composite/multi-component materials over large composition ranges, which are otherwise very difficult if not impossible to obtain via any other technique. For example, composite coatings of Copper and ZnO can be obtained over a range of 0.01% to >50 atomic % of Copper in the coating. Moreover, composite coatings containing both $TiO_2$ and ZnO can be obtained over a vast compositional range from approximately 1% of $TiO_2$ in ZnO to approximately 1% of ZnO in $TiO_2$.

Embodments combining both conformal solution-phase coating methods and conformal vapor phase coating methods: Combining solution-phase methods with vapor phase methods allows coating embodiments that cannot be obtained by the individual methods alone and that can produce antimicrobial surfaces with very large surface areas and high antimicrobial efficacies.

In one such embodiment, aluminum oxide ($Al_2O_3$) nanotubes can be obtained by Anodization as a first layer on the assembly. Anodization of aluminum and aluminum oxide surfaces to create ordered $Al_2O_3$ nanotubes/pores is the only known non-lithography-based technique known to create such structures of $Al_2O_3$. Such structures are obtained by use of certain electrolyte chemistries and certain regimes of applied voltage/current during the anodization process. The surface of nanotubes (nanopores to a slightly lesser degree) offers an effective surface area that can be orders of magnitude larger (10× to >1000×) than a smooth surface of aluminum oxide. However, $Al_2O_3$ is not known to display appreciable antimicrobial efficacy. But by using vapor deposition techniques, particularly ALD, PE-ALD, or PA-ALD, a second coating of a highly antimicrobial material such as Copper or ZnO or $TiO_2$ or $WO_3$ or others can be applied very conformally on the nanotubes of $Al_2O_3$, thus forming an antimicrobial surface with an effective surface area about 10× to >1000× larger than a smooth surface of the same material. In other words, a surface with anodized $Al_2O_3$ nanotubes (or any other type of non-antimicrobial material nanotubes/nanopores such as Si nanotubes/nanopores) can be used as a super high surface area template for the subsequent deposition of ANY/ALL antimicrobial material(s) via vapor phase techniques ALD or CVD. Thus, such a combination of anodization+vapor phase coating processes offers a unique method by which super high surface area antimicrobial coatings can be obtained for ANY/ALL known antimicrobial materials.

Anodization processes may generate nanotubes/nanopores for several oxides, both non-antimicrobial (such as Al2O3), and antimicrobial (such as TiO2, WO3, etc.).

In another embodiment, a first coating of ZnO nanotubes/nanopores can be applied using Anodization, followed by a second coating of Copper applied by ALD techniques, thus forming unique and novel composite antimicrobial surfaces with an extremely large antimicrobial surface area. In this embodiment a combination of solution-based coating (anodization)+a second coating by vapor phase. However, the difference here compared to the previous Al2O3-based embodiment is that in this case both the coated materials are antimicrobial. Thus, such a method offers a unique way to create composite or alloyed-antimicrobial materials. One can in theory make hundreds of material combinations. Other embodiments are at least TiO2 nanotubes+Cu, TiO2 nanotubes+Ag, WO3 nanotubes+Cu, WO3 nanotubes+Ag, TiO2 nanotubes+conformal ZnO (doped or undoped), WO3 nanotubes+conformal ZnO or conformal TiO2 (doped or undoped). The basic embodiment being the enablement of super high surface area composite antimicrobial coatings by the use of a combination of solution-based and vapor-phase coating methods.

Non-antimicrobial nanotube template (Al2O3, Si)+Alloyed antimicrobial coating via ALD, i.e., the ALD deposition would include 2 or more antimicrobial materials in the film (in comparison, #1 is a single-component second coating via ALD/CVD). Examples: Cu-doped ZnO2, or TiO2-doped ZnO via ALD.

3-step coatings: Examples: [a] Anodized $Al_2O_3$+Electroplated Cu+ALD ZnO (the latter two materials are antimicrobial). [b] A glass or plastic assembly coated with a $1^{st}$ coating of Zinc oxide ZnO (or $TiO_2$ or $WO_3$) via ALD+a $2^{nd}$ process step Anodization to convert the smooth ALD coating to nanotubes/high surface area without changing the coating chemistry+a $3^{rd}$ step where a $2^{nd}$ antimicrobial material like Cu is coated on the nanotube/nanopore surface via ALD or CVD or even Electrodeposition The embodiments herein are unique and can only be achieved by this combination of solution+vapor phase coating techniques.

Post-Coating Annealing Methods. Post-coating treatment, for example, such as thermal annealing treatments, and can be applied to further optimize coatings for antimicrobial efficacy. Coating/film properties such as chemical phase, crystal structure, grain size, grain orientation, defect density, dopant incorporation, etc., can be modified by thermal annealing in the about 60° C.-800° C. range. The gas chemistry during annealing can also be varied to obtain the desired result.

In one embodiment, annealing in an oxygen atmosphere improves the oxygen stoichiometry in sub-stoichiometric $TiO_{(2-x)}$ or $WO_{(3-x)}$ or $ZnO_{(1-x)}$ to $TiO_2$, $WO_3$, or ZnO respectively. The efficacy of this process will at least depend on the partial pressure of the oxidizing gas (O2, O3, N2O, H2O, etc.), the temperature of the annealing, and the time of annealing. In another embodiment, the desired mixture of the three phases of $TiO_2$, rutile, anatase and brookite, can be obtained by annealing in air. This embodiment is an example where annealing is used to obtain the desired crystal phases and phase mixtures of the antimicrobial material.

In another embodiment, annealing in a nitrogen atmosphere incorporates nitrogen as a dopant in semiconducting oxides, for e.g., $TiO_{(2-x)}N_x$ can be formed. This embodiment uses annealing for doping, to enhance the antimicrobial sensitivity. In another embodiment annealing in a reducing gas, for example, such as hydrogen, removes oxygen from Copper that might have been oxidized during coating, thus obtaining a purer metallic Copper, thus increasing antimicrobial activity. Moreover, hydrogen annealing can be used to deliberately introduce sub-stoichiometry in oxides to form $TiO_{(2-x)}$ or $WO_{(3-x)}$ or $ZnO_{(1-x)}$ to reduce their energy band gap and thus increase their antimicrobial activity.

Figure 9A:
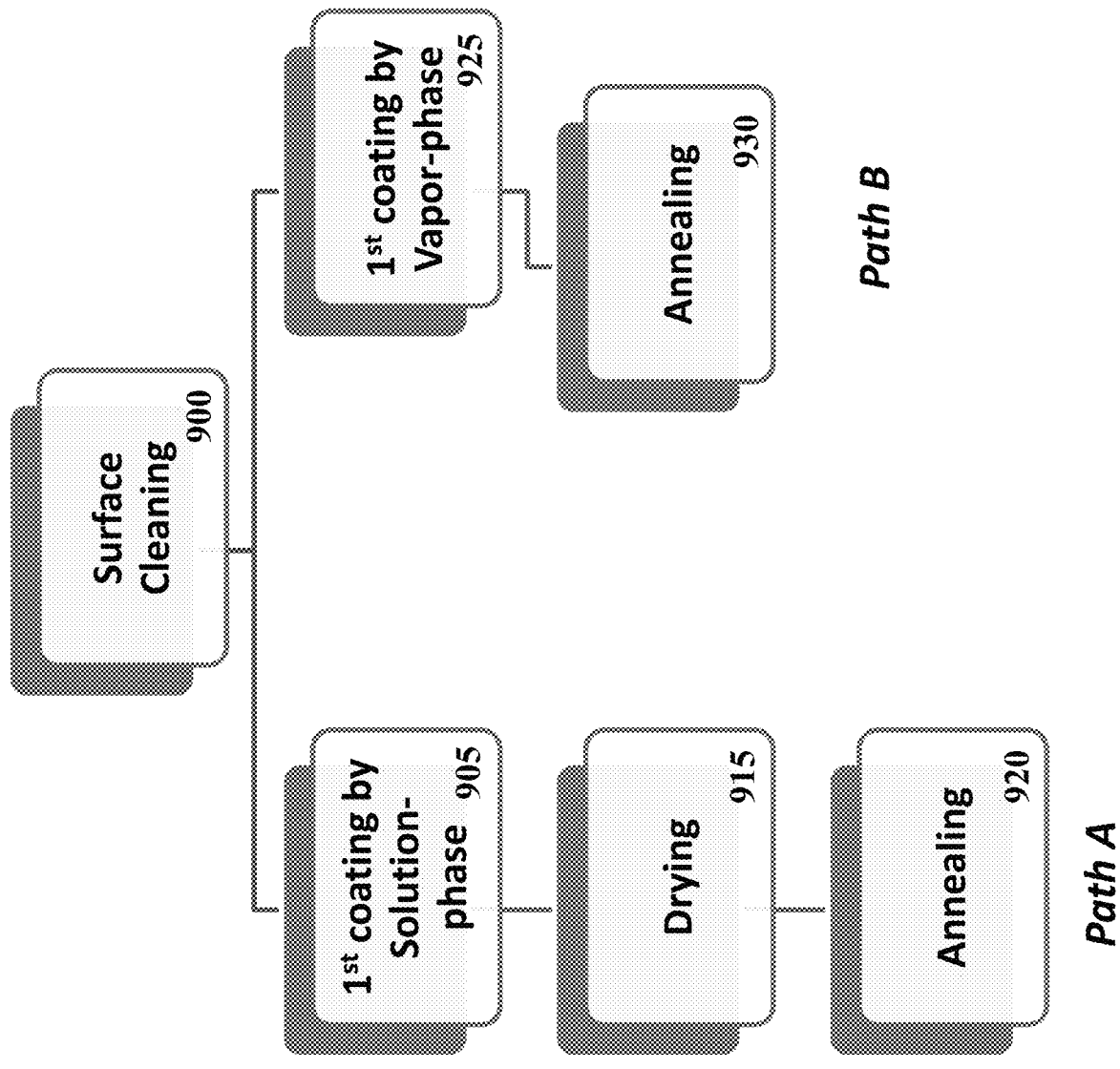
FIG. 9A illustrates an example flowchart of at least 2 Coating Paths to form antimicrobial coatings, with respect to 1-Step Coating methods, according to some embodiments.

FIG. 9A is a flowchart illustration of at least 2 Coating Paths to form antimicrobial coatings, with respect to 1-Step Coating methods, with basic steps of these paths depicted. The coating process method can follow any one of the two paths (A and B) shown; however, other combinations of sub steps as well as new sub steps may be developed from the concepts laid out herein.

Path A may include a Surface Cleaning step 900, then a $1^{st}$ Coating by Solution-phase step 905, then a Drying step 915, then an Annealing step 920. The details of each step may include the teachings contained herein, as well as the incorporated references, and what a person of normal skill in the art would thoughtfully do. Some embodiments of Path A are: [1] Anodization of a titanium or titanium alloy substrate to form antimicrobial TiO2 or TiO(2-x) nanotubes/nanopores; [2] Electrodeposition of a Copper-Zinc composite coating on stainless steel, followed by an annealing treatment that increases the surface area by encouraging Cu to agglomerate.

Path B may include a Surface Cleaning step 900, then a $1^{st}$ Coating by Vapor-phase step 925, and then an Annealing step 930. The details of each step may include the teachings contained herein, as well as the incorporated references, and what a person of normal skill in the art would thoughtfully do. As taught above, some embodiments of Path B are: [1] Deposition of antimicrobial Zinc oxide by ALD on a porcelain ceramic substrate; [2] Deposition of antimicrobial Cu by ALD on a glass substrate.

Figure 9B:
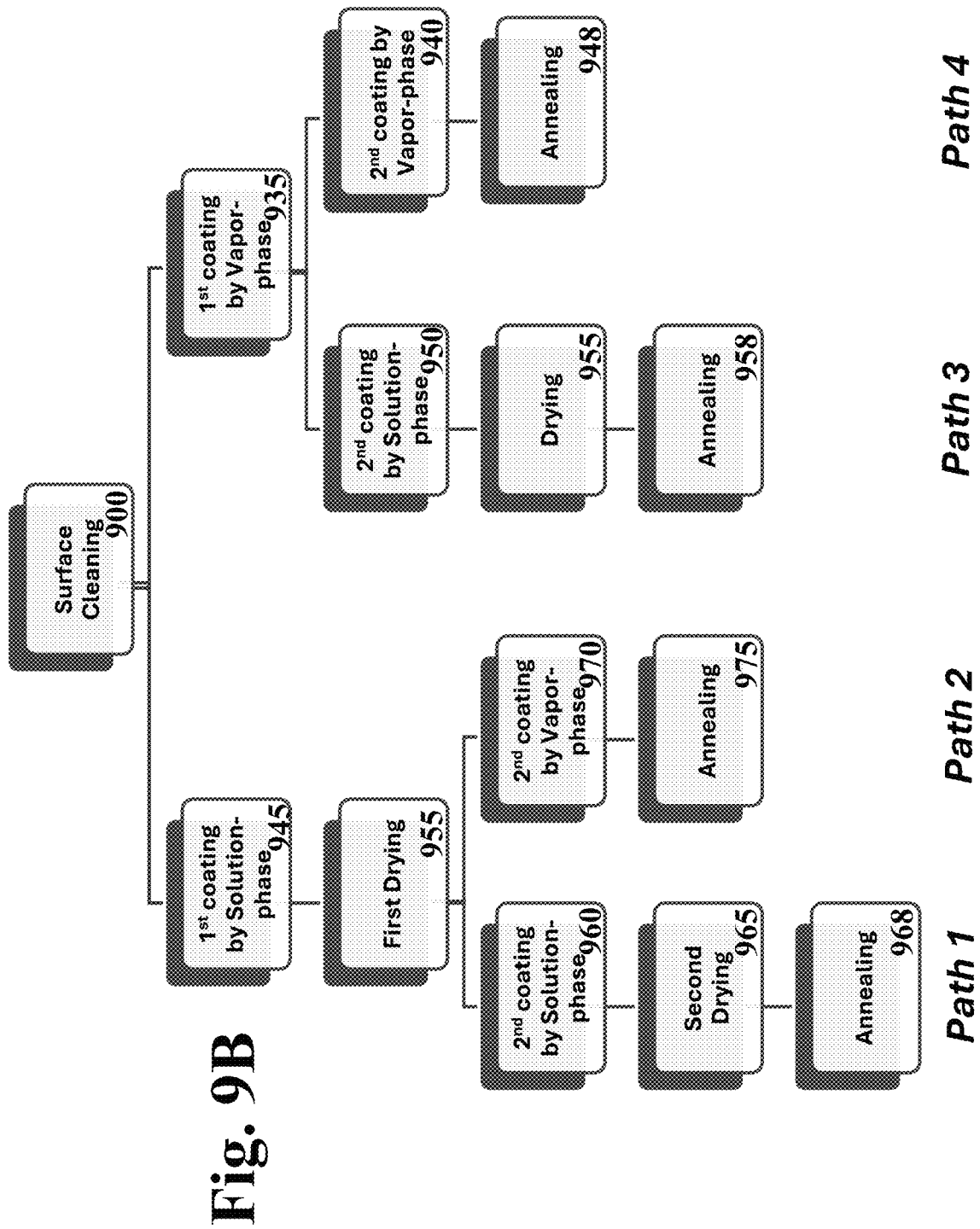
FIG. 9B illustrates an example flowchart of at least 4 Coating Paths to form antimicrobial coatings, with respect to 2-Step (or greater than 2-Step) Coating methods, according to some embodiments.

FIG. 9B is a flowchart illustration of at least 4 Coating Paths to form antimicrobial coatings, with respect to 2-Step (or more than 2) Coating methods, with basic steps of these paths depicted. The coating process method can follow any one of the four paths shown; however, other combinations of sub steps as well as new sub steps may be developed from the concepts laid out herein. Furthermore, more than two coating steps could be used in some embodiments.

Path 1 may include a Surface Cleaning step 900, then a $1^{st}$ Coating by Solution-phase step 945, then a First Drying step 955, then a $2^{nd}$ coating by Solution-phase step 960, then a Second Drying step 965, and then an Annealing step 968. The details of each step may include the teachings contained herein, as well as the incorporated references, and what a person of normal skill in the art would thoughtfully do. Two examples of Path 1 are Anodized $Al_2O_3$+Electroplated Copper OR Anodized $TiO_2$+Electroplated Copper. Annealing would improve the adhesion of Cu to the $Al_2O_3$.

Path 2 may include a Surface Cleaning step 900, then a $1^{st}$ Coating by Solution-phase step 945, then a First Drying step 955, then a $2^{nd}$ coating by Vapor-phase step 970, and then an Annealing step 975. The details of each step may include the teachings contained herein, as well as the incorporated references, and what a person of normal skill in the art would thoughtfully do. As taught above, an example of a Path 2 is as follows: provide a first coating of ZnO nanotubes/nanopores which can be applied using Anodization, followed by a second coating of Copper which may be applied by ALD techniques.

Path 3 may include a Surface Cleaning step 900, then a $1^{st}$ Coating by Vapor-phase step 935, then a $2^{nd}$ coating by Solution-phase step 950, then a Drying step 955, and then an Annealing step 958. The details of each step may include the teachings contained herein, as well as the incorporated references, and what a person of normal skill in the art would thoughtfully do. An example of Path 3 is as follows: coating a glass or plastic assembly via a 181 ALD coating of an antimicrobial oxide such as, for example, $TiO_2$, ZnO or $WO_3$. This is followed by a $2^{nd}$ step where the smooth ALD coating is converted to a high surface area nanotube surface via anodization without changing the chemistry/composition of the $1^{st}$ ALD coating. The annealing step in this case may be an Oxidation anneal to improve the stoichiometry of the oxide, or a Doping annealing where, for example, N2 is incorporated in the oxide to enhance its antimicrobial efficacy.

Path 4 may include a Surface Cleaning step 900, then a $1^{st}$ Coating by Vapor-phase step 935, then a $2^{nd}$ coating by Vapor-phase step 940, and then an Annealing step 948. The details of each step may include the teachings contained herein, as well as the incorporated references, and what a person of normal skill in the art would thoughtfully do. The following is an example of Path 4: provide a $1^{st}$ coating of an antimicrobial oxide such as, for example, TIO2, ZnO, WO3 via ALD/CVD, followed by a $2^{nd}$ coating of an antimicrobial metal such as, for example, Cu, also via ALD/CVD. In this case Annealing would be used to make a surface with a controlled roughness of Copper as in at least FIG. 12.

Detailed Description: Compositions and Nanostructures of Antimicrobial Coatings

The coating materials and methods described above can be used to obtain a variety of coating compositions and nanostructures offering varying degrees of antimicrobial efficacies, as well as varying degrees of dependence on UVA/Visual artificial lighting for their efficacy. Some embodiments are shown in FIG. 10 to FIG. 14. Additional embodiments can be constructed by using the concepts and methods described in at least herein.

Figure 10:
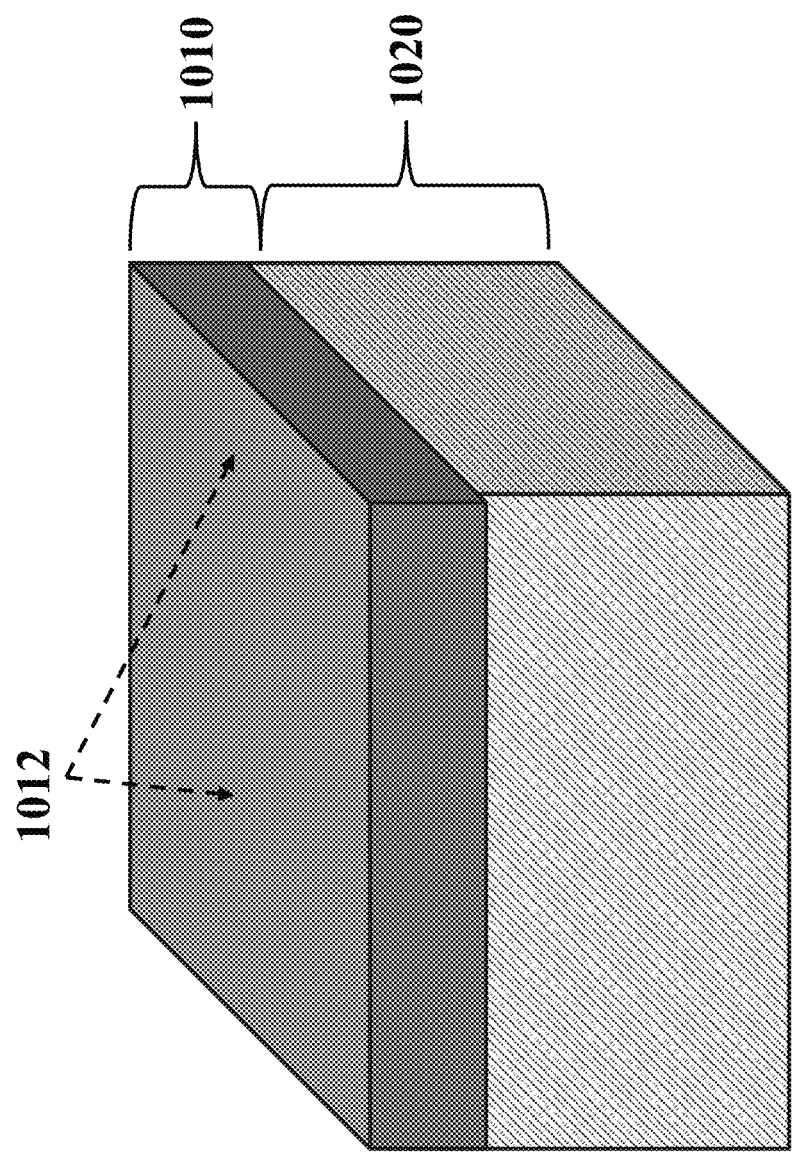
FIG. 10 illustrates an example of a 1-phase Smooth Antimicrobial Coating layer which may include a smooth antimicrobial coating material affixed to an Antimicrobial Assembly Surfaces, according to some embodiments.

FIG. 10 is an example illustration of a 1-phase Smooth Antimicrobial Coating layer 1010 which may include smooth antimicrobial coating material 1012 affixed to Antimicrobial Assembly Surfaces 1020. Smooth antimicrobial coating material 1012 may include chemistries such as ZnO, Cu, $TiO_2$, $WO_3$, $C_3N_4$, and the like. Antimicrobial Assembly Surfaces 1020 may include inner tube, outer tube, fins, baffles and other surfaces and structures desired to provide the maximum effective antimicrobial material area exposed to the air/fluid passing thru the antimicrobial assembly. Smooth antimicrobial coating material 1012 thickness can range at least from about 10 nano-meters to about 10 micro-meters.

Figure 11:
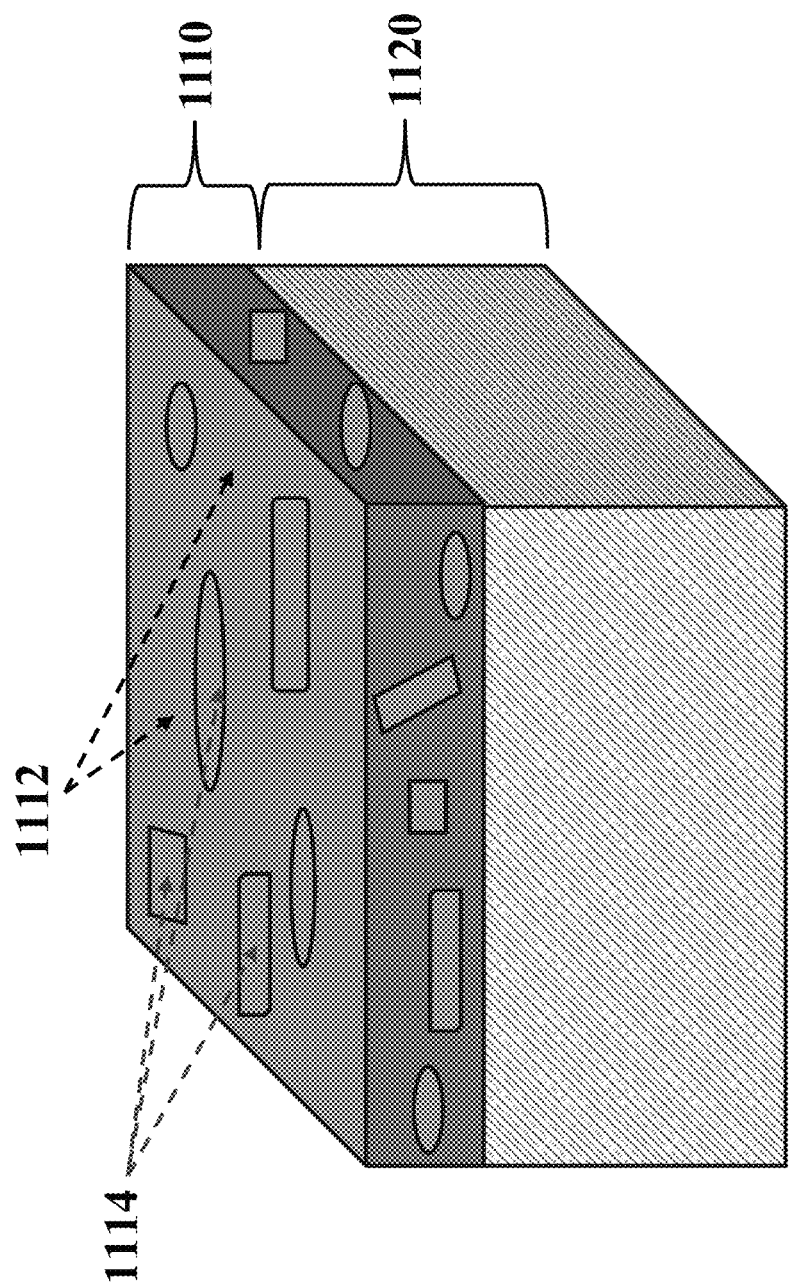
FIG. 11 illustrates an example of a 2-phase Smooth Antimicrobial Coating layer which may include a first smooth antimicrobial coating material and a second smooth antimicrobial coating material, both or one may be directly affixed to Antimicrobial Assembly Surfaces, according to some embodiments.

FIG. 11 is an example illustration of a 2-phase Smooth Antimicrobial Coating layer 1110 which may include First smooth antimicrobial coating material 1112 and Second smooth antimicrobial coating material 1114, both or one may be directly affixed to Antimicrobial Assembly Surfaces 1120. First smooth antimicrobial coating material 1112 and Second smooth antimicrobial coating material 1114 may include chemistries such as $ZnO+TiO_2$, $ZnO+Cu$, $TiON+Ag$, $WO_3+ZnO$, $C_3N_4+Cu$, and the like.

Antimicrobial Assembly Surfaces 1120 may include inner tube, outer tube, fins, baffles and other surfaces and structures desired to provide the maximum effective antimicrobial material area exposed to the air/fluid passing thru the antimicrobial assembly. Antimicrobial Assembly Surfaces 1120 may include the elements and components of at least field deployable antimicrobial assemblies with reference numbers 200s, 300s, 400s, 500s, 600s, and 700s described herein. First smooth antimicrobial coating material 1112 and Second smooth antimicrobial coating material 1114 thicknesses can each or in total range at least from about 10 nano-meters to about 10 micro-meters. The surface of the Antimicrobial Assembly Surfaces 1120 may be roughened and/or etched such that there is a nano-disordered upon which the smooth coatings may affix to, thus increasing the effective area of the antimicrobial material(s) which may increase the antimicrobial efficacy.

Figure 12:
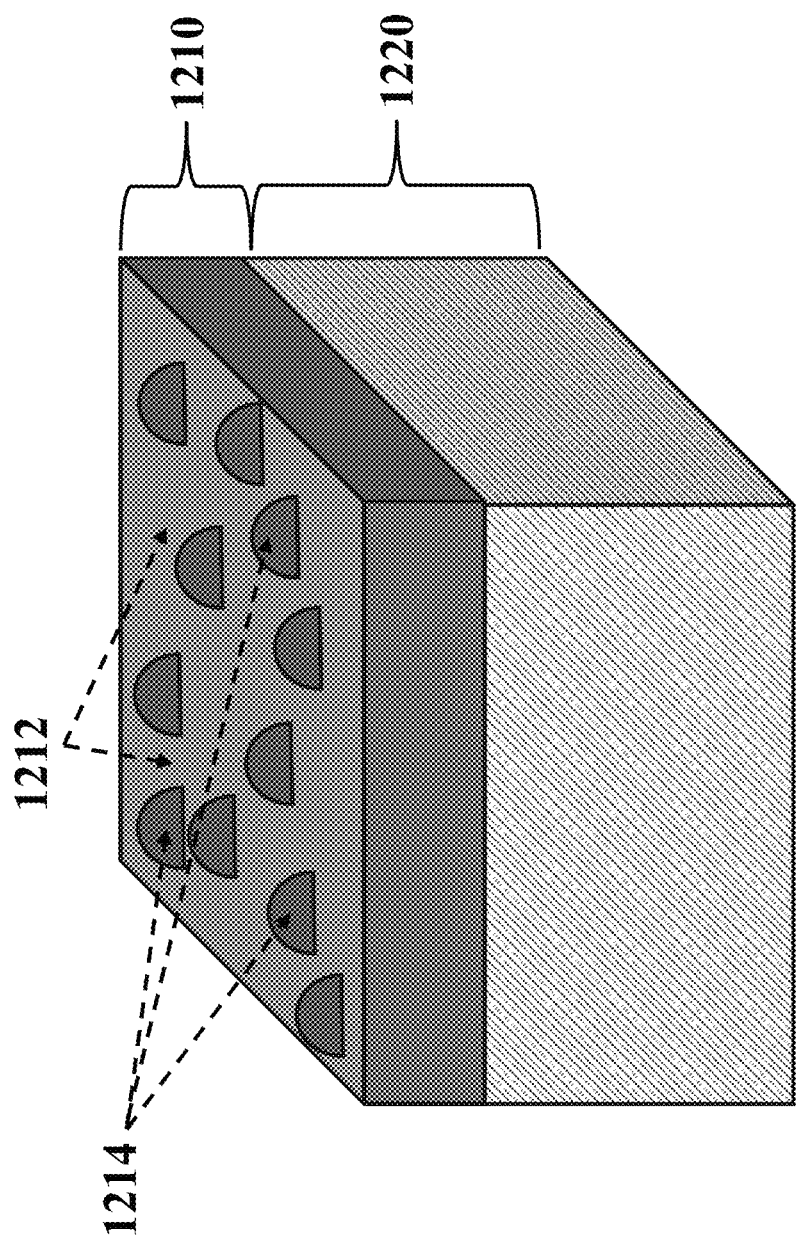
FIG. 12 illustrates an example of a 2-phase engineered roughness Antimicrobial Coating layer which may include a first antimicrobial coating material and a second antimicrobial coating material, both or one may be directly affixed to Antimicrobial Assembly Surfaces, according to some embodiments.

FIG. 12 is an example illustration of a 2-phase Antimicrobial Coating layer with engineered roughness 1210 which may include First antimicrobial coating material 1212 and Second antimicrobial coating material 1214, both or one may be directly affixed to Antimicrobial Assembly Surfaces 1220. First antimicrobial coating material 1212 and Second antimicrobial coating material 1214 may include chemistries such as, for example, Cu on $TiO_2$, ZnO on $TiO_2$, $WO_3$ on Cu, and the like. One or both of First antimicrobial coating material 1212 and Second antimicrobial coating material 1214 may be engineered to provide a rough surface, i.e. a disordered nanostructure, which increases the antimicrobial surface area thus increasing efficacy. Path 4 generally applies here. Copper is a softer metal and Cu thin films are known to agglomerate with annealing. Thus, the surface roughness may be engineered by co-optimization of the Cu film thickness+annealing conditions. The exact recipe will depend on the thickness of Cu, the substrate material, the temperature, and atmosphere of annealing.

Antimicrobial Assembly Surfaces 1220 may include inner tube, outer tube, fins, baffles and other surfaces and structures desired to provide the maximum effective antimicrobial material area exposed to the air/fluid passing thru the antimicrobial assembly. Antimicrobial Assembly Surfaces 1220 may include the elements and components of at least field deployable antimicrobial assemblies with reference numbers 200s, 300s, 400s, 500s, 600s, and 700s described herein. First antimicrobial coating material 1212 and Second antimicrobial coating material 1214 thicknesses can each or in total range at least from about 10 nano-meters to about 10 micro-meters. Moreover, additionally the surface of the Antimicrobial Assembly Surfaces 1220 may itself be roughened and/or etched such that there is a nano-disordered upon which the engineered rough coatings may affix to, thus increasing the effective area of the antimicrobial material(s) which may increase the antimicrobial efficacy.

Very high antimicrobial surface areas are possible by engineering ordered nanostructures obtained from single-coating methods such as Anodization, or double coating methods such as Electrodeposition+Anodization, or Dip-coating+Anodization, or Anodization+ALD, or triple-coating methods such as Electrodeposition+Anodization+ALD. Two examples are described herein, but many more are possible. Dis-ordered nanostructures are useful as well, but do not maximize the antimicrobial surface area as ordered nanostructures provide. Nanotubes (NT) are illustrated in at least FIG. 13 and FIG. 14, however, NT's represent an approximation of the desired or possible nanostructures and other types and styles of nanostructures may be formed to increase the anti-microbial surface area when compared to the absence of those nanostructures.

Figure 13:
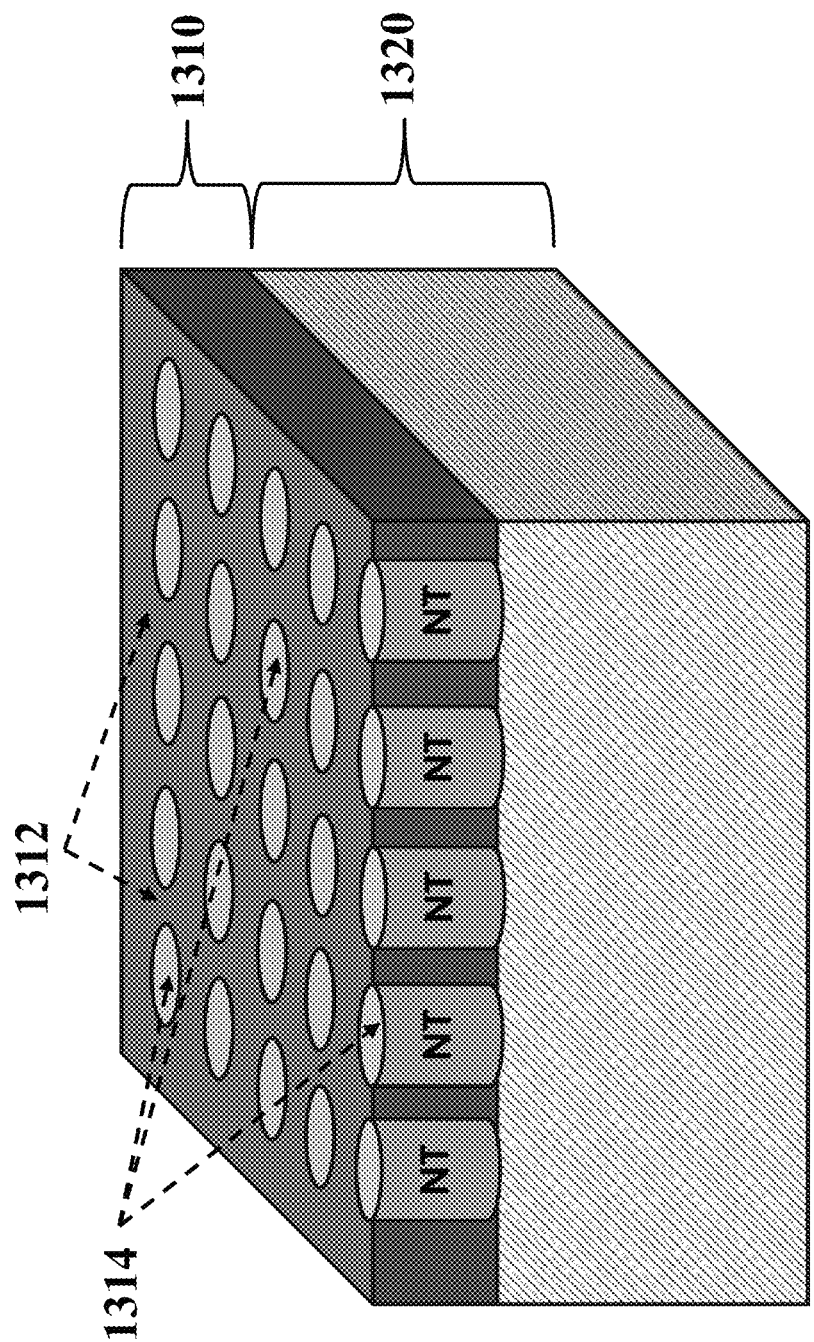
FIG. 13 illustrates an example of a 1-phase Ordered Nanostructured Antimicrobial Coating layer which may include anodized nanostructures which may include ordered nanotubes or nanopores formed within, both or one may be directly affixed to Antimicrobial Assembly Surfaces, according to some embodiments.

FIG. 13 is an example illustration of a 1-phase Ordered Nanostructured Antimicrobial Coating layer 1310 which may include Anodized nanostructure 1312 which may include ordered nanotubes or nanopores (or similar nanostructures) 1314 formed within, both or one may be directly affixed to Antimicrobial Assembly Surfaces 1320. Anodized nanostructure 1312 may include antimicrobial chemistries such as ZnO, $TiO_2$, $WO_3$, and the like. FIG. 13 is an example of a 1-step coating method, which is not covered in FIG. 9. FIG. 9 illustrates 2-step methods.

Antimicrobial Assembly Surfaces 1320 may include inner tube, outer tube, fins, baffles and other surfaces and structures desired to provide the maximum effective antimicrobial material area exposed to the air/fluid passing thru the antimicrobial assembly. Antimicrobial Assembly Surfaces 1320 may include the elements and components of at least field deployable antimicrobial assemblies with reference numbers 200s, 300s, 400s, 500s, 600s, and 700s described herein. Anodized nanostructure 1312 and ordered nanotubes or nanopores 1314 may have thicknesses/depths at least from about 50 nano-meters to about 100,000 nano-meters. Diameters of ordered nanotubes or nanopores 1314 may include at least about 20 nano-meters to about 250 nano-meters. Spacing between ordered nanotubes or nanopores 1314 may include at least about 10 nano-meters to about 250 nano-meters. Ordered nanotubes or nanopores 1314 have inner surfaces exposed so that the air/fluid of interest may access the increased surface area of the approximately cylindrical surface of Anodized nanostructure 1312 and accordingly an increase the antimicrobial efficacy. The bottom end of ordered nanotubes or nanopores 1314 may expose the Antimicrobial Assembly Surfaces 1320 or may rather expose additional surfaces of antimicrobial active Anodized nanostructure 1312.

Figure 14:
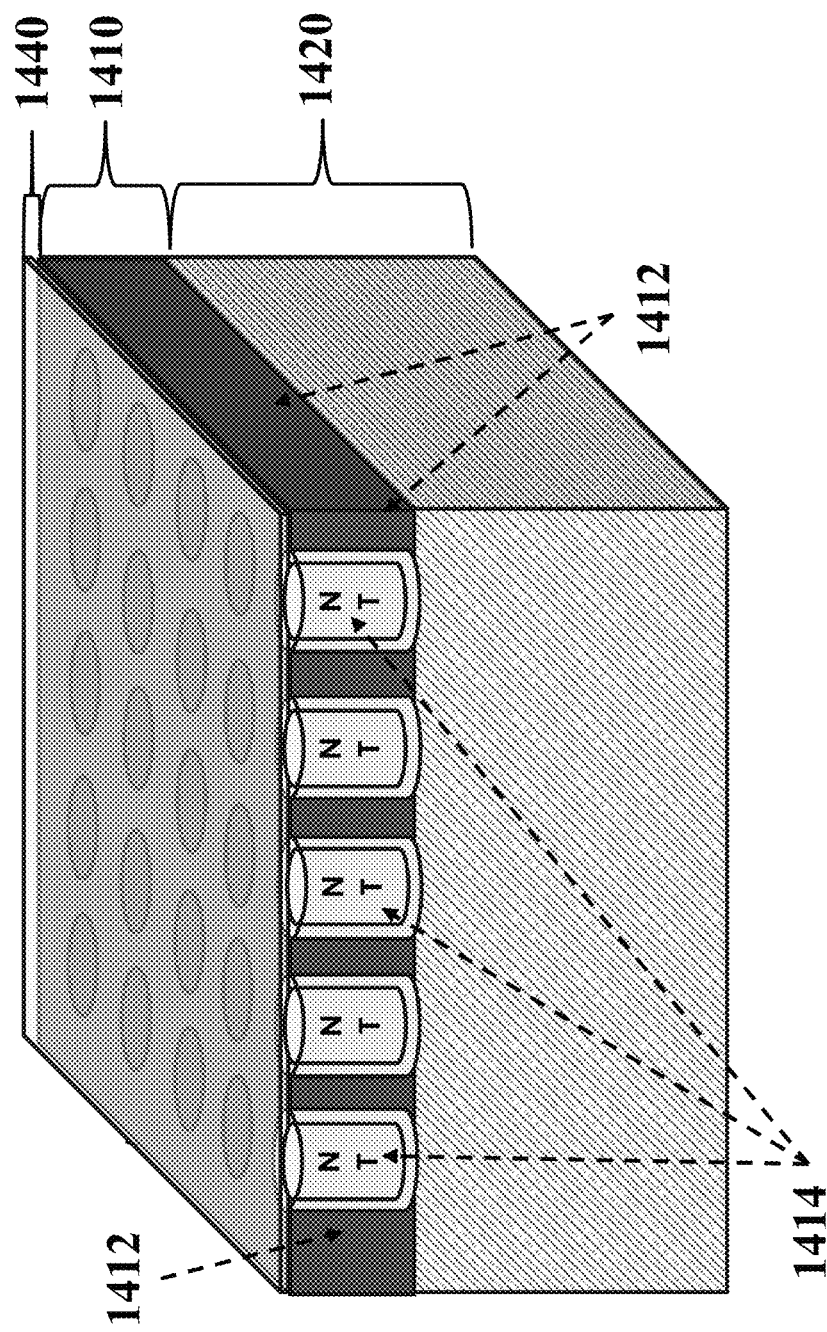
FIG. 14 illustrates an example of a double or triple coating Ordered Nanostructured Antimicrobial Coating layer which may include an anodized nanostructure which may include ordered nanotubes or nanopores formed within, both or one may be directly affixed to Antimicrobial Assembly Surfaces, according to some embodiments.

FIG. 14 is an example illustration of a double or triple coating Ordered Nanostructured Antimicrobial Coating layer 1410 which may include Anodized nanostructure 1412 which may include ordered nanotubes or nanopores (or similar nanostructures) 1414 formed within, both or one may be directly affixed to Antimicrobial Assembly Surfaces 1420. Double or triple coating Ordered Nanostructured Antimicrobial Coating layer 1410 may further include an ALD deposited antimicrobial film 1440 in a second and/or third coating process, which may coat and adhere to the inner surfaces of the ordered nanotubes or nanopores (or similar nanostructures) 1414. Anodized nanostructure 1410 and ALD deposited antimicrobial film 1440 may include antimicrobial chemistries such as $Al_2O_3$+ZnO, $TiO_2$+ZnO, $Al_2O_3$+Cu, $WO_3$+Cu, $TiO_2$+Ag, and the like. These are some examples of Paths 1 and 2.

Antimicrobial Assembly Surfaces 1420 may include inner tube, outer tube, fins, baffles and other surfaces and structures desired to provide the maximum effective antimicrobial material area exposed to the air/fluid passing thru the antimicrobial assembly. Antimicrobial Assembly Surfaces 1420 may include the elements and components of at least field deployable antimicrobial assemblies with reference numbers 200s, 300s, 400s, 500s, 600s, and 700s described herein. Anodized nanostructure 1412 and ordered nanotubes or nanopores 1414 may have thicknesses/depths at least from about 50 nano-meters to about 100,000 nano-meters. Diameters of ordered nanotubes or nanopores 1414 may include at least about 20 nano-meters to about 250 nano-meters. Spacing between ordered nanotubes or nanopores 1414 may include at least about 10 nano-meters to about 250 nano-meters. Ordered nanotubes or nanopores 1414 have inner surfaces exposed so that the air/fluid of interest may access the increased surface area of the approximately cylindrical surface of Anodized nanostructure 1412 and accordingly an increase the antimicrobial efficacy. The bottom end of ordered nanotubes or nanopores 1414 may expose the Antimicrobial Assembly Surfaces 1420 or may rather expose additional surfaces of antimicrobial active ALD deposited antimicrobial film 1440.

Furthermore, depending on the transmissibility of the antimicrobial coating employed, the outer surface of inner tube 330 and the interior of outer antimicrobial (AM) tube 310 may be coated with a transmissible antimicrobial coating and the exterior of outer antimicrobial (AM) tube 310 may be coated with an absorptive antimicrobial material (or the same material as used on the outer surface of inner tube 230), depending on engineering, cost, and efficiency considerations. Furthermore, depending on the transmissibility of the antimicrobial coating employed, the outer surface of inner tube 230 may be coated with a transmissible antimicrobial coating and the interior of outer antimicrobial (AM) tube 210 may be coated with an absorptive antimicrobial material (or the same material as used on the outer surface of inner tube 230), depending on engineering, cost, and efficiency considerations.

RELATED DISCLOSURES AND REFERENCES

HEPA filters: https://en.wikipedia.org/wiki/HEPA
UVGI: https://en.wikipedia.org/wiki/Ultraviolet_germicidal_irradiation
Water chlorination: https://www.health.com/side-effects-of-chlorine-on-your-body-7494539#:~;text=Chlorine%20can%20irritate%20the%20eyes, also%20irritate%20the%20respirat ory%20system.
Water chlorination: https://en.wikipedia.org/wiki/Water_chlorination\
PCO filters+UVGI systems: 1. https://ultravation.com/uv-catalyst/ 2. https://airhealth.com/havenplus-whole-house-air-purifier/
CDC website ventilator-associated pneumonia: https://www.cdc.gov/hai/vap/vap.html
Mold in HVAC: https://www.hvac.com/expert-advice/mold-in-hvac-systems-and-ductwork/
Diarrhea: 1. UNICEF: https://data.unicef.org/topic/child-health/diarrhoeal-disease/ 2. WHO: https://www.who.int/news-room/fact-sheets/detail/diarrhoeal-disease
Bacterial infection California trout: https://caltrout.org/news/cdfw-euthanizes-3-2-million-trout-to-halt-bacteria-outbreak
Antimicrobial Copper: 1. https://www.antimicrobialcopper.com/antimicrobial-efficacy 2. https://www.antimicrobial-copper.com/evidence-and-studies Some scientific papers on antimicrobial materials:
Soni, V., et al., "Current perspective in metal oxide based photocatalysts for virus disinfection: A review," *J. of Environmental Management*, 308 (2022) 114617.
Abhinandan, K., et al., "The practicality and prospects for disinfection control by photocatalysis during and post pandemic: A critical review," *Environmental Research*, 209 (2022) 112814.
Dimapilis, E. A. S., et al., "Zinc oxide nanoparticles for water disinfection," *Sustainable Environmental Research*, 28 (2018) pp. 47-56.
Bharti, et al., "A review on the capability of zinc oxide and iron oxides nanomaterials, as a water decontaminating agent: adsorption and photocatalysis," *Applied Water Science*, (2022) 12:46.
Pasquale, I.D., et al., "TiO2-based nanomaterials assisted photocatalytic treatment for virus inactivation: perspectives and applications," *Current Opinion in Chemical Engineering* 2021, 34:100716.
Salah, I., et al., "Copper as an antimicrobial agent: recent advances," *RSC Adv.*, 2021, 11, 18179.

Comments on Detectability of the taught, described, disclosed and suggested invention(s):

Detection & infringement of the assemblies can be carried out by reverse engineering, visual inspection, etc.

Detection of the composition/chemistry and morphology/microstructure/nanostructure of the coatings can be carried out using standard microscopy and chemical analysis techniques including scanning electron microscopy (SEM), transmission electron microscopy (TEM), energy dispersive x-ray analysis (EDX), electron energy loss spectroscopy (EELS), Rutherford backscattering (RBS), secondary ion mass spectroscopy (SIMS), mass spectroscopy (MS, ICPMS), x-ray photoelectron spectroscopy (XPS), auger electron spectroscopy (AES), x-ray fluorescence (XRF), and so on.

Detectability of the materials processing steps used to fabricate and apply coatings can be deduced but not fully confirmed by microscopy and chemical analysis.

CONCLUSION

Although the present embodiments have been described with reference to specific example embodiments, various modifications and changes can be made to these embodiments without departing from the broader spirit and scope of the various embodiments. Accordingly, the specification and drawings are to be regarded in an illustrative rather than a restrictive sense.

We claim:
1. A field-deployable antimicrobial assembly designed for gases or liquids, the assembly comprising:
 a substrate,
 a first material in contact with at least one surface of said substrate,
  wherein said first material comprises nanotubes and/or nanopores, and
  wherein said nanotubes and/or nanopores are open on one end only; and
 a second material deposited on at least a majority of surfaces of said nanotubes and/or nanopores, wherein said second material comprises at least one antimicrobial material, and
wherein said second material inactivates biological microorganisms in gases and liquids upon physical contact.

2. The assembly according to claim 1,
wherein said substrate comprises a metal, and
wherein said metal comprises aluminum.

3. The assembly according to claim 1,
wherein said first material comprises aluminum oxide ($Al_2O_3$).

4. The assembly according to claim 1,
wherein said second material is at least one of the following:
   i. copper, Cu; or
   ii. silver, Ag; or
   iii. titanium dioxide, TiO2 (doped or undoped); or
   iv. titanium sub-oxides, TiO(2-x), or
   v. zinc oxide, ZnO (doped or undoped); or
   vi. tungsten oxide, $WO_3$; or
   vii tungsten sub-oxides, WO(3-x).

5. The assembly according to claim 1,
wherein said first material comprises at least one antimicrobial material.

6. The assembly according to claim 1,
wherein said second material is deposited using vapor phase coating methods Atomic Layer Deposition (ALD) and/or Chemical Vapor Deposition (CVD).

7. The assembly according to claim 1,
wherein said second material comprises at least one composite film of antimicrobial semiconducting materials and antimicrobial metals.

8. A field-deployable antimicrobial assembly designed for gases or liquids, the assembly comprising:
a substrate,
a first material in contact with at least one surface of said substrate,
   wherein said first material comprises nanotubes and/or nanopores,
   wherein said nanotubes and/or nanopores are open on one end only, and
   wherein said first material comprises at least one first antimicrobial material; and
a second material deposited on at least a majority of surfaces of said nanotubes and/or nanopores,
   wherein said second material comprises at least one second antimicrobial material, and
   wherein said at least one first antimicrobial material and said at least one second antimicrobial material inactivate biological microorganisms in gases and liquids upon physical contact.

9. The assembly according to claim 8,
wherein said substrate comprises a metal, and
wherein said metal comprises copper.

10. The assembly according to claim 8,
wherein said first material is copper (Cu), copper II oxide (CuO), or copper III oxide ($Cu_2O_3$).

11. The assembly according to claim 8,
wherein said second material is at least one of the following:
   i. copper, Cu; or
   ii. silver, Ag; or
   iii. titanium dioxide, TiO2 (doped or undoped); or
   iv. titanium sub-oxides, TiO(2-x), or
   v. zinc oxide, ZnO (doped or undoped); or
   vi. tungsten oxide, $WO_3$; or
   vii. tungsten sub-oxides, WO(3-x).

12. The assembly according to claim 8,
wherein said second material is deposited using vapor phase coating methods Atomic Layer Deposition (ALD) and/or Chemical Vapor Deposition (CVD).

13. The assembly according to claim 8,
wherein said second material comprises at least one composite film of antimicrobial semiconducting materials and antimicrobial metals.

14. A method of forming a high surface area antimicrobial material, the method comprising:
providing a substrate;
forming a first material on top of or within said substrate,
   wherein said first material is formed by solution-based coating,
   wherein said first material comprises nanotubes and/or nanopores, and
   wherein said nanotubes and/or nanopores are open on one end only; and
forming a second material,
   wherein said second material is disposed on a majority of surfaces of said nanotubes and/or nanopores,
   wherein said second material is formed by a vapor-phase coating process, and
   wherein said second material is antimicrobial, and
   wherein said second material inactivates biological microorganisms in gases and liquids upon physical contact.

15. The method according to claim 14,
wherein said substrate compromises a metal,
wherein said solution-based coating is anodization of said metal.

16. The method according to claim 14,
wherein said first material comprises at least one antimicrobial material.

17. The method according to claim 14, further comprising:
an anneal,
   wherein said anneal is performed after said second material is formed.

18. The method according to claim 14, further comprising:
an anneal,
   wherein said second material comprises at least one composite film of antimicrobial semiconducting materials and antimicrobial metals, and
   wherein said anneal is performed after said second material is formed.

19. The method according to claim 14,
wherein said second material is at least one of the following:
   i. copper, Cu; or
   ii. silver, Ag; or
   iii. titanium dioxide, TiO2 (doped or undoped); or
   iv. titanium sub-oxides, TiO(2-x), or
   v. zinc oxide, ZnO (doped or undoped); or
   vi. tungsten oxide, $WO_3$; or
   vii. tungsten sub-oxides, WO(3-x).

20. The method according to claim 14,
wherein said second material is deposited using Atomic Layer Deposition (ALD) and/or Chemical Vapor Deposition (CVD).

* * * * *